United States Patent
Kuhl

(10) Patent No.: US 10,287,643 B2
(45) Date of Patent: May 14, 2019

(54) BLAST FURNACE AND METHOD FOR OPERATING A BLAST FURNACE

(71) Applicant: CCP Technology GmbH, Munich (DE)

(72) Inventor: Olaf Kuhl, Greifswald (DE)

(73) Assignee: CCP TECHNOLOGY GMBH, Munich (DE)

( * ) Notice: Subject to any disclaimer, the term of this patent is extended or adjusted under 35 U.S.C. 154(b) by 227 days.

(21) Appl. No.: 15/039,444

(22) PCT Filed: Nov. 27, 2014

(86) PCT No.: PCT/EP2014/075798
§ 371 (c)(1),
(2) Date: May 26, 2016

(87) PCT Pub. No.: WO2015/078962
PCT Pub. Date: Jun. 4, 2015

(65) Prior Publication Data
US 2017/0002433 A1    Jan. 5, 2017

(30) Foreign Application Priority Data
Nov. 28, 2013 (DE) .................... 10 2013 018 074

(51) Int. Cl.
*C21B 5/06* (2006.01)
*C21B 5/00* (2006.01)
(Continued)

(52) U.S. Cl.
CPC ............... *C21B 5/06* (2013.01); *B01D 53/62* (2013.01); *B01D 53/84* (2013.01);
(Continued)

(58) Field of Classification Search
CPC .......... B01D 2251/20; B01D 2257/502; B01D 2257/504; B01D 2258/025; B01D 53/62;
(Continued)

(56) References Cited

U.S. PATENT DOCUMENTS

| 3,884,677 A | 5/1975 | Wenzel et al. |
| 2011/0209576 A1 | 9/2011 | Roth et al. |
| 2014/0364516 A1 | 12/2014 | Kuhl |

FOREIGN PATENT DOCUMENTS

| CN | 101555533 | 10/2009 |
| DE | 1928981 | 12/1970 |

(Continued)

OTHER PUBLICATIONS

JP-60159104-A. Machine translation of the description. (Year: 1985).*

*Primary Examiner* — Jenny R Wu
(74) *Attorney, Agent, or Firm* — Tarolli, Sundheim, Covell & Tummino LLP

(57) ABSTRACT

A process for processing metal ore includes: reducing a metal ore, particularly a metallic oxide, in a blast furnace shaft; producing furnace gas containing $CO_2$, in the blast furnace shaft; discharging the furnace gas from the blast furnace shaft; directing at least a portion of the furnace gas directly or indirectly into a $CO_2$-converter; and converting the $CO_2$ contained in the furnace gas into an aerosol consisting of a carrier gas and C-particles in the $CO_2$-converter in the presence of a stoichiometric surplus of C; directing at least a first portion of the aerosol from the $CO_2$-converter into the blast furnace shaft; and introducing $H_2O$ into the blast furnace shaft. By virtue of the reaction $C+H_2O \rightarrow CO_2 + 2H$, nascent hydrogen is produced in the blast furnace which causes rapid reduction of the metal ore. The speed of reduction of the metal ore is thus increased, and it is possible to increase either the throughput capacity of the blast furnace or to reduce the size of the blast furnace. An aerosol in the form of a fluid is easily introducible into the blast furnace shaft.

12 Claims, 8 Drawing Sheets

(51) Int. Cl.
| | |
|---|---|
| *H01M 8/22* | (2006.01) |
| *B01D 53/84* | (2006.01) |
| *C12M 1/02* | (2006.01) |
| *C12P 7/08* | (2006.01) |
| *B01D 53/90* | (2006.01) |
| *B01D 53/86* | (2006.01) |
| *C21B 7/00* | (2006.01) |
| *C12M 1/00* | (2006.01) |
| *B01D 53/62* | (2006.01) |
| *H01M 8/0612* | (2016.01) |
| *C12P 7/06* | (2006.01) |

(52) U.S. Cl.
CPC ......... *B01D 53/8671* (2013.01); *B01D 53/90* (2013.01); *C12M 21/12* (2013.01); *C12M 41/20* (2013.01); *C12M 43/04* (2013.01); *C12M 47/20* (2013.01); *C12P 7/06* (2013.01); *C12P 7/08* (2013.01); *C21B 5/003* (2013.01); *C21B 5/004* (2013.01); *C21B 7/002* (2013.01); *H01M 8/0612* (2013.01); *H01M 8/22* (2013.01); *B01D 2251/20* (2013.01); *B01D 2257/502* (2013.01); *B01D 2257/504* (2013.01); *B01D 2258/025* (2013.01); *C21B 2005/005* (2013.01); *C21B 2100/02* (2013.01); *C21B 2100/22* (2017.05); *C21B 2100/24* (2017.05); *C21B 2100/282* (2017.05); *H01M 2250/10* (2013.01); *Y02A 50/2358* (2018.01); *Y02B 90/14* (2013.01); *Y02C 10/02* (2013.01); *Y02C 10/04* (2013.01); *Y02E 50/17* (2013.01); *Y02P 10/122* (2015.11); *Y02P 10/128* (2015.11); *Y02P 10/265* (2015.11); *Y02P 10/283* (2015.11); *Y02P 20/152* (2015.11); *Y02P 20/59* (2015.11); *Y02P 70/56* (2015.11)

(58) Field of Classification Search
CPC .... B01D 53/84; B01D 53/8671; B01D 53/90; C12M 21/12; C12M 41/20; C12M 43/04; C12M 47/20; C12P 7/06; C12P 7/08; C21B 2005/005; C21B 2100/02; C21B 2100/22; C21B 2100/24; C21B 2100/282; C21B 5/003; C21B 5/004; C21B 5/06; C21B 7/002; H01M 2250/10; H01M 8/0612; H01M 8/22; Y02A 50/2358; Y02B 90/14; Y02C 10/02; Y02C 10/04; Y02E 50/17; Y02P 10/122; Y02P 10/128; Y02P 10/265; Y02P 10/283; Y02P 20/152; Y02P 20/59; Y02P 70/56
See application file for complete search history.

(56) References Cited

FOREIGN PATENT DOCUMENTS

| | | | |
|---|---|---|---|
| GB | 1317826 | | 5/1973 |
| JP | 50154109 | | 12/1975 |
| JP | 60159104 | A * | 8/1985 |
| JP | 2003064407 | | 3/2003 |
| WO | 0006671 | | 2/2000 |
| WO | 2014198635 | | 12/2014 |

* cited by examiner

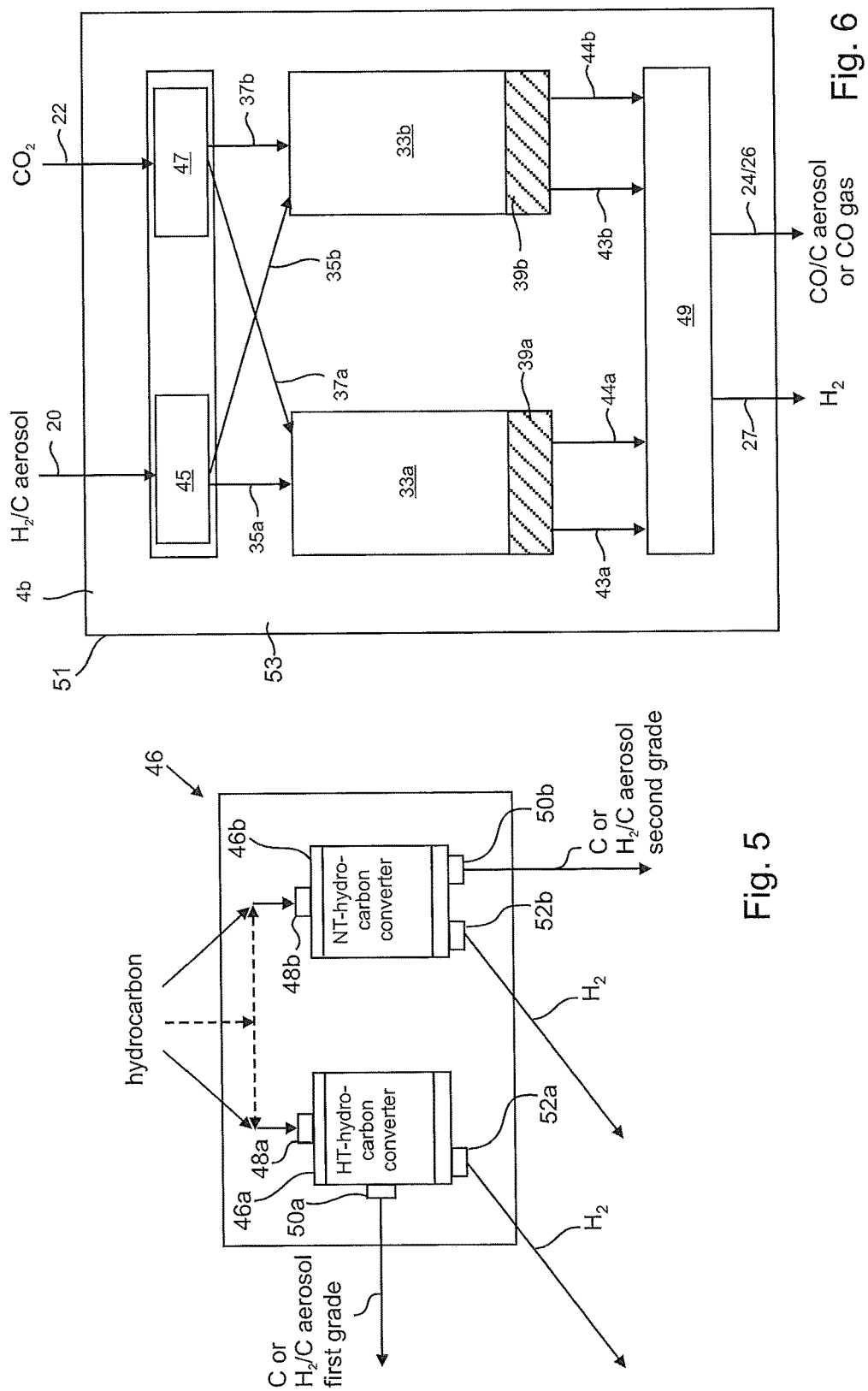

BLAST FURNACE AND METHOD FOR OPERATING A BLAST FURNACE

RELATED APPLICATIONS

This application corresponds to PCT/EP2014/075798, filed Nov. 27, 2014, which claims the benefit of German Application No. 10 2013 018 074.0, filed Nov. 28, 2013, the subject matter of which are incorporated herein by reference in their entirety.

BACKGROUND OF THE INVENTION

The present invention relates to a blast furnace and a method for operating a blast furnace which may be employed for increasing the capacity or the throughput.

Metallurgical plants are plants for processing metal ore, wherein the central element of such a metallurgical plant is a blast furnace. These metallurgical plants have been known for a long time. A blast furnace is fed with raw materials which comprise metal ore, additives and heating material. Usually coal or coke is used as a heating material, wherein coal and coke produce heat by burning in the presence of air on the one hand and wherein coal and coke also function as reduction agents for the metal ore since the metal ore is basically comprised of metal oxide. When reducing metal ore in a blast furnace, various gases are produced, these being collectively known as furnace gas or flue gas. Said furnace gas usually contains a substantial amount of carbon dioxide ($CO_2$). Carbon dioxide is a greenhouse gas and in recent years more and more effort has been made to prevent greenhouse gases or to convert them, as these greenhouse gases are regarded as being detrimental to the climate.

In the field of metal production, it is a general aim to use as few raw materials and heating materials as possible, as these materials are expensive and it is expensive to transport them. Much effort has been made to reduce the amount of coke/coal used in the production process. One approach was blowing coal dust into the blast furnace, and another approach was producing carbon monoxide as a reduction gas, either in the blast furnace itself or in a separate gasification reactor outside the blast furnace. From EP 09318401 A1, it is known to blow a portion of the carbon required for reducing the metal ore into the blast furnace in the form of a substitute reduction material. In this sense, e.g. natural gas, heavy oil, fine coal and similar materials having a high carbon content may be used as a substitute reduction material. These materials may be directly blown into the blast furnace shaft or may be gasified outside of the blast furnace shaft in a separate gasification reactor so as to form a reduction gas. Subsequently, such a reaction gas may be directed into the blast furnace shaft. The method known from EP 09318401 A1 may provide a possibility to reduce the amount of coal or coke consumed and enable materials that are difficult to process to be made use of as a substitute reduction material, but the problem of high $CO_2$ emission in the metal production process has not been solved.

From the post-published German patent application No. 10 2013 009 993, there is known a blast furnace and a method for processing metal ore which are suitable for reducing $CO_2$ emissions at high throughputs and reducing the quantity of additives and heating materials compared with metallurgical plants used in former times. Furthermore, DE 10 2004 036 767 B4 discloses a method for producing pig iron in a blast furnace which is operated with $CO_2$-free furnace gas that is fed-back to the furnace with added oxygen and hydrocarbons. DE 1 928 981 A1, describes a method for producing pig iron in a blast furnace wherein the furnace gas is freed of dust whereafter hydrocarbons are added. The furnace gas is then heated and fed back into the blast furnace. From WO 2012/085 449 A1, there is known a method for producing pig iron in a blast furnace wherein $CO_2$ is removed from the furnace gas which is then fed back into the blast furnace shaft.

The present invention is directed toward a blast furnace and a method for operating a blast furnace which are suitable for reducing $CO_2$ emissions at high throughputs and wherein the quantity of additives and heating materials are reduced compared with metallurgical plants used at present. Furthermore, the capacity of the blast furnace is to be increased.

SUMMARY OF THE INVENTION

The object of the present invention is achieved by a method for processing metal ores which comprises the following steps: reducing a metal ore, especially a metal oxide in a blast furnace shaft; producing furnace gas containing $CO_2$ in the blast furnace shaft; discharging the furnace gas from the blast furnace shaft; directing at least a portion of the furnace gas directly or indirectly into a $CO_2$-converter and converting the $CO_2$ contained in the furnace gas into an aerosol consisting of a carrier gas and C-particles in the $CO_2$-converter in the presence of a stoichiometric surplus of C. A first portion of the aerosol from the $CO_2$-converter is directed into the blast furnace shaft. A second portion of the aerosol from the $CO_2$-converter is directed to a further processing process. Depending upon the construction of the $CO_2$-converter, there is a greater quantity of aerosol and/or CO resulting from the $CO_2$ conversion process which is not needed in the blast furnace shaft for the reduction of metal ore. The additionally produced aerosol and/or CO can thus be used as a raw material or source of energy in a further processing process. Alternatively, the second part of the aerosol from the $CO_2$-converter is burned first to form a $CO_2$-containing exhaust gas mixture before it is passed on in the form of this exhaust gas mixture to a further processing process. The aerosol produced can thus be used as a source of energy. Depending upon the implementation of the further processing process, it is desirable to provide the $CO_2$ as a raw material. Further, water vapour $H_2O$ is directed into the blast furnace shaft and the introduction of the aerosol and the introduction of the water vapour into the blast furnace shaft is effected via separate nozzles. Thus, optimised nozzles for introducing the aerosol and introducing the water vapour can be provided but nevertheless rapid reduction by nascent hydrogen can be achieved. Nascent hydrogen which causes rapid partial reduction of the metal ore is thus produced in the blast furnace by the reaction $C+H_2O \rightarrow CO+2H$. The speed of reduction of the metal ore is thereby increased and it is possible to either increase the throughput capacity of the blast furnace or reduce the size of the blast furnace. It is easy to introduce an aerosol in the form of a fluid into the blast furnace shaft. The further processing process is one of the following. The further processing process may be an oxidation process in a fuel cell or a combustion process in a gas engine or a gas turbine. By means of these processes, heat or mechanical power can be extracted from the combustible portions of the aerosol or CO gas mixture issuing from the $CO_2$-converter. The further processing process may be a biological conversion process in a bio converter which is carried out using microbes or algae according to one or more of the following net equations: a) $6CO+3H_2O \rightarrow C_2H_5OH+4CO_2$; b) $6H_2+2CO_2 \rightarrow C_2H_5OH+3H_2O$; c) $2CO+$ $4H_2 \rightarrow C_2H_5OH+H_2O$. Consequently, CO and in particular the unwanted $CO_2$ in the atmosphere can be converted into ethanol by the addition of hydrogen. By suitable choice of the microbes or algae, kerosene, diesel, gasoline, methanol or other fuels can also be produced. In this embodiment, the further processing process is a biological conversion process in a bio converter and, when using microbes or algae, the introduced gases CO and $CO_2$ are converted into kerosene, diesel, gasoline, methanol or another fuel as the end-product. The further processing process may also be a conversion process in which synthesis gas is converted into a functionalised and/or non-functionalised hydrocarbon, preferably paraffin, kerosene, diesel, gasoline, liquid gases or methanol. Thus a saleable product may be produced from the large quantities of CO gas which result directly or in the form of a carrier gas of a CO/C aerosol and which are not needed for the reduction of metal ore in the blast furnace shaft.

In another embodiment of the method, some water vapour $H_2O$ is added to the aerosol before directing it into the blast furnace shaft. Preferably thereby, as much water vapour $H_2O$ is added to the aerosol as is required to a produce a hydrogen-poor synthesis gas $CO/H_2$ before it is directed into the blast furnace. A gas serving as a reducing agent which can easily be introduced into the blast furnace shaft is thus produced.

In accordance with a further embodiment of the method wherein the furnace gas is routed indirectly to the $CO_2$-converter, it is first burned to form a $CO_2$-containing exhaust gas mixture before being passed on in the form of this exhaust gas mixture to the $CO_2$-converter and is then converted in the $CO_2$-converter. Thus, the CO contained in the furnace gas and other inflammable constituents are used as a source of energy.

Depending upon the implementation of the further processing process, it is advantageous if a portion of the $CO_2$-containing exhaust gas mixture bypasses the $CO_2$-converter and is directed to a further processing process in order to provide $CO_2$ thereto as a raw material.

In one embodiment of the method, a portion of the furnace gas is passed on directly, i.e. it bypasses the $CO_2$-converter, to a further processing process. A larger quantity of $CO_2$ can thereby be provided to the further processing process. It is also possible to provide a gas mixture having a desired ratio of CO to $CO_2$ for the further processing process.

Preferably, a portion of the aerosol is introduced into the blast furnace shaft in a lower region above the surface of the molten bath, in particular, in an area comprising the blast gas entry point. The aerosol can thus be directed as a reducing agent into the reduction zone of the blast furnace shaft. Moreover, when converting an existing blast furnace so as to operate according to the process being described here, the previously existing blast jets can be used as inlets for the aerosol.

A portion of the aerosol is preferably directed to one or more aerosol introduction points located along the blast furnace shaft. The conversion processes in the different zones of the blast furnace shaft can thereby be affected and the process well controlled.

The aerosol introduction points are also optionally located partly below the surface of the molten bath in the blast furnace shaft. A reduction process can thus be achieved in the molten metal if required.

In one embodiment of the method, additional carbon is introduced into the lower region of the blast furnace shaft in contact with the molten bath in order to lower the melting point of the metal.

In one embodiment of the method, the conversion of $CO_2$ into an aerosol in the $CO_2$-converter takes place at a temperature of 800 to 1700° C. Under these conditions, establishment of the Boudouard equilibrium is achieved and by virtue of which a high proportion of the introduced $CO_2$ is converted into CO. Hereby, an aerosol comprising C-particles is then produced if a molar surplus of $CO_2$ is added. A catalyst is not necessary thereby.

Preferably, the $CO_2$-converter comprises a plurality of alternately operative converter chambers, wherein the conversion of $CO_2$ in a first converter chamber is implemented with a stoichiometric surplus of C so that an aerosol with C-particles is formed; and wherein the conversion of $CO_2$ in a second converter chamber is implemented with a stoichiometric equilibrium of C and $CO_2$ or with a stoichiometric surplus of $CO_2$ so that a CO gas or a $CO_2/CO$ gas mixture without C-particles is formed. By means of the $CO_2$-converter, a $H_2/C$-aerosol can be converted uninterruptedly into an aerosol incorporating C-particles, into a CO gas or into a $CO_2/CO$ gas mixture without C-particles and a high degree of conversion of the materials introduced into the converter is achieved.

Advantageously thereby, the $CO_2$-converter comprises a plurality of converter chambers which can be filled between a desired minimum and a desired maximum particle-filling level, wherein the conversion of the $CO_2$ contained in the furnace gas into an aerosol comprises the following steps: supplying a first part of the converter chambers with a $H_2/C$-aerosol consisting of hydrogen and carbon-containing particles until the converter chambers being supplied are filled to the desired maximum particle-filling level; supplying a second part of the converter chambers with the $H_2/C$-aerosol as soon as the desired maximum particle-filling level of the first part of the converter chambers is reached; and directing $CO_2$ into the first part of the converter chambers that is filled with carbon-containing particles, wherein the carbon is converted into carbon monoxide according to the equation $C+CO_2 \rightarrow 2CO$. By means of the $CO_2$-converter according to this embodiment, a $H_2/C$-aerosol can likewise be converted uninterruptedly into an aerosol incorporating C-particles, into a CO gas or into a $CO_2/CO$ gas mixture without C-particles and a high degree of conversion of the materials being introduced into the converter is achieved.

Preferably, when the further processing process is a biological conversion process, the method comprises the following further steps: decomposing a fluid containing hydrocarbon into carbon and hydrogen, a) by means of a plasma or b) by introducing thermal energy, wherein the decomposing step is preferably carried out in a separate hydrocarbon converter; and supplying said hydrogen $H_2$ to the biological conversion process. Hot carbon for the reduction of the $CO_2$ in the Boudouard equilibrium is thereby provided from the furnace gas or from the exhaust gas of the combustion machine mentioned above. Furthermore, larger quantities of hydrogen are provide thereby making it possible for the biological conversion process to produce large quantities of ethanol and little or no $CO_2$.

Preferably, when implementing the method in which the further processing process is a conversion process for the conversion of synthesis gas, the synthesis gas is produced by the following steps: decomposing a fluid containing hydrocarbons into carbon C and hydrogen $H_2$ a) by means of a plasma or b) by introducing thermal energy; and mixing at least a portion of the hydrogen $H_2$ with at least a portion of the CO component in the aerosol that was produced in the $CO_2$-converter. Thus, large quantities of hydrogen may be produced. Preferably, the fluid containing hydrocarbons is a low cost fluid, such as $CH_4$, crude oil or other heavy oils.

If, in the course of the method, more than one different further processing process is effected, the resultant mass flows of furnace gas, exhaust gas, C, CO gas, $H_2$ gas, $CO_2$ gas can be used optimally.

Preferably, the blast furnace shaft and/or the $CO_2$-converter is additionally heated. Since, in the method being described here, the heating of the blast furnace shaft by coke/coal can be reduced or avoided, the thermal energy in the blast furnace shaft may possibly not be sufficient in every situation for reaching the adequately high temperatures that are needed for the reduction of the metal ore and for melting the metal.

Preferably, the additional heating process is implemented at least partly with the heat resulting from the combustion steps described above and/or with the heat which ensues from one of the steps of decomposing a fluid containing hydrocarbon to form carbon C and hydrogen $H_2$ with the assistance a) of a plasma or b) by adding thermal energy and/or with heat which ensues from the conversion of CO into functionalised or non-functionalised hydrocarbons. Consequently, the heat arising from the decomposing process can be further used locally in a process requiring constant heat and so is not wasted.

In a further embodiment of the method, the additional heating process comprises directly heating the raw metal by means of induction. Thus, only energy is introduced into the magnetic components i.e. into the metal which, after all, is going to be produced in the blast furnace shaft.

The carrier gas of the aerosol which is produced in the $CO_2$-converter consists, in all the embodiments of the method, of CO or of a mixture of CO and $H_2$.

Furthermore, the object is achieved by a blast furnace for metal production which comprises the following: a blast furnace shaft having a first furnace gas outlet and at least one aerosol inlet; a $CO_2$-converter which comprises at least one converter chamber, a $CO_2$-converter inlet and a $CO_2$-converter gas inlet for gases containing $CO_2$ and is adapted to convert $CO_2$ into an aerosol consisting of a carrier gas and C-particles; wherein the first furnace gas outlet is directly or indirectly connected to the $CO_2$-converter gas inlet; wherein the $CO_2$-converter comprises at least one first aerosol outlet serving as a converter outlet for discharging a first portion of the aerosol produced in the $CO_2$-converter, wherein said first aerosol outlet is directly or indirectly connected to the blast furnace shaft. Further, the $CO_2$-converter comprises at least one second aerosol outlet serving as a converter outlet means for removing a second portion of the aerosol. Depending upon the construction of the $CO_2$-converter, this then results in a further amount of aerosol and/or CO from the process for the conversion of the $CO_2$ which is not needed in the blast furnace shaft for the reduction of metal ore. The additionally resulting aerosol and/or CO can therefore be used in a further processing process as raw material or as a source of energy. The $CO_2$-converter also comprises at least one $H_2O$-inlet via which $H_2O$ can be introduced into the blast furnace shaft. The aerosol inlet for introducing the aerosol and the $H_2O$ inlet for introducing $H_2O$ into the blast furnace shaft are separate inlets. Optimised nozzles for introducing the aerosol and introducing the water vapour can thus be provided but nevertheless rapid reduction by nascent hydrogen can be achieved. Thus, by means of the reaction $C+H_2O \rightarrow CO+2H$, nascent hydrogen, which effects rapid partial reduction of the metal ore, can be produced in the blast furnace. Consequently, the speed of reduction of the metal ore is increased and it is thereby possible to either increase the throughput capacity of the blast furnace or reduce the size of the blast furnace. An aerosol in the form of a fluid is easy to introduce into the blast furnace shaft. Further, at least one of the converter outlets of the $CO_2$-converter is connected to the further processing converter. The components of the aerosol or CO gas mixture produced in the $CO_2$-converter which cannot be fed back and used in the blast furnace shaft can be converted into heat, mechanical power or into end-products in the further processing converter. The heat and/or mechanical power can be used for operating the blast furnace. The end-products can be sold. The further processing converter may be one of the following. The further processing converter may be a gas engine, a gas turbine or a fuel cell. Heat or mechanical power can be extracted from the inflammable $H_2$ or CO gas by means of these machines. The further processing converter may also be a bio converter in which a conversion process using microbes or algae is carried out according to one or more of the following net equations: a) $6CO+3H_2O \rightarrow C_2H_5OH+4CO_2$; b) $6H_2+2CO_2 \rightarrow C_2H_5OH+3H_2O$; c) $2CO+4H_2 \rightarrow C_2H_5OH+H_2O$ Consequently, CO and especially the unwanted $CO_2$ can be converted into ethanol by the addition of hydrogen. By suitable choice of the microbes or algae, kerosene, diesel, gasoline, methanol or some other fuel can also be produced. In this embodiment, the further processing converter is a bio converter in which a conversion process takes place utilising microbes or algae so that kerosene, diesel, gasoline, methanol or some other fuel are produced as the end-product. Further, the further processing converter may be a CO converter which is adapted to produce functionalised and/or non-functionalised hydrocarbons with the assistance of a synthesis gas. The hydrocarbons are preferably, paraffin, kerosene, diesel, petroleum, liquid gases or methanol. A saleable product can thus be extracted from the large quantities of CO gas being produced. In this embodiment, the synthesis gas is advantageously a mixture of hydrogen from the hydrocarbon converter and CO from the $CO_2$-converter.

In another embodiment of the blast furnace, at least one $H_2O$-inlet for the introduction of $H_2O$ is arranged with the aerosol inlet in such a way that $H_2O$ is mixed with the aerosol before being introducing into the blast furnace shaft. Preferably thereby, as much water vapour $H_2O$ is added to the aerosol as is needed to produce hydrogen-poor synthesis gas $CO/H_2$ before the introduction thereof into the blast furnace. Consequently, a reducing agent in the form of a gas is produced and this can easily be introduced into the blast furnace shaft.

The $CO_2$-converter of the blast furnace preferably comprises the following: at least one aerosol converter inlet for a $H_2/C$-aerosol consisting of hydrogen and carbon-containing particles; at least one converter gas inlet for a $CO_2$-containing gas; at least two converter outlets; at least two converter chambers which can be filled with particles between a desired minimum and a desired maximum particle-filling level; at least one diverting device which can selectively connect a part of the converter chambers to or can separate it from a) at least one of the aerosol converter inlets for the $H_2/C$-aerosol or b) at least one of the converter gas inlets for the $CO_2$-containing gas; at least one lead-out device which can connect a part of the converter chambers to at least one of the converter outlets or separate it therefrom. With the aid of a $CO_2$-converter according to this embodiment, a $H_2/C$-aerosol can likewise be converted uninterruptedly into a CO/C aerosol with C-particles, into a CO gas or into a $CO_2$/CO gas mixture without C-particles and a high degree of conversion of the materials introduced into the converter can be achieved.

Preferably, a heatproof filter and especially a wire filter or a ceramic filter is arranged in the converter chambers of the $CO_2$-converter. These are reliable components which can withstand the high temperatures of more than 800° C.

The $CO_2$-converter preferably comprises a plurality of converter chambers in order to optimise both the generation of aerosol for the blast furnace shaft as well as gas mixtures for the further processing converter. Advantageously, the converter chambers have a tubular shape and are arranged in parallel one another in the form of a bank of tubes. The tubular shape has a cylindrical, triangular, square or hexagonal cross section in the longitudinal direction in order to achieve good thermal transmission properties and a simple manufacturing process. The converter chambers can thus also be adapted to surrounding structures by which they can likewise be heated, especially if the C-converter is operated together with a plasma-operated or thermal-energy-operated hydrocarbon converter.

In one embodiment of the $CO_2$-converter, clearance spaces are formed between the converter chambers, and a fluid can be fed through the clearance spaces thereby enabling a heat exchange process to take place between a fluid in the converter chambers and a fluid in the clearance spaces. If the furnace gas or the $CO_2$-containing exhaust gas serving as this fluid is fed through the clearance spaces before being directed into the converter chambers, then these gases will be pre-heated thereby contributing to a saving of energy when the system is in operation. If, in operation, liquid water is injected into the clearance spaces, water vapour can be produced and introduced into the blast furnace shaft. Since the converter chambers have a temperature of several 100s of degrees Celsius, the liquid water is vaporised into steam.

In accordance with one embodiment, the blast furnace comprises a combustion machine having a combustion machine inlet and at least one exhaust gas outlet for emitting a $CO_2$-containing exhaust gas. At least one of the converter outlets of the $CO_2$-converter is connected to the combustion machine inlet of the combustion machine, and the combustion machine is operated at least partially with inflammable constituents of the aerosol or gas mixture produced in the $CO_2$-converter. One of the exhaust gas outlets of the combustion machine is connected to a further processing converter. An aerosol having inflammable constituents that is produced in the $CO_2$-converter or a CO gas mixture can be used as sources of energy in the combustion machine. Depending upon the type of the further processing process, it is desirable to make the $CO_2$-containing exhaust gas of the combustion machine available as a raw material.

In one exemplary embodiment, a filter which is suitable for trapping particles can be arranged between the $CO_2$-converter and the combustion machine. This is a useful feature if the combustion machine cannot process C-particles from the $CO_2$-converter.

In accordance with one embodiment, the blast furnace comprises a combustion machine with a combustion gas inlet and at least one exhaust gas outlet for emitting a $CO_2$-containing exhaust gas. In this case, there is an indirect connection between the furnace gas outlet and the $CO_2$-converter, and the first furnace gas outlet of the blast furnace shaft is connected to the combustion gas inlet of the combustion machine. The combustion machine is operated at least partially with furnace gas. The CO contained in the furnace gas and other inflammable components can thus be used as energy sources. In this embodiment, one of the exhaust gas outlets of the combustion machine is preferably connected to the $CO_2$-converter gas inlet of the $CO_2$-converter in order to direct a portion of the $CO_2$-containing exhaust gas mixture into the $CO_2$-converter.

Depending upon the type of the further processing process, it is advantageous for one of the exhaust gas outlets of the combustion machine to be connected to the further processing converter in order to guide a portion of the $CO_2$-containing exhaust gas mixture past the $CO_2$-converter to the further processing process. A larger quantity of $CO_2$ can therefore be made available to the further processing process. It is also possible to produce a gas mixture having a desired ratio of CO to $CO_2$ for the further processing process.

Depending upon the type of the further processing process, it is advantageous for the blast furnace to comprise a second furnace gas outlet which is connected directly to the further processing converter, i.e. it by-passes the $CO_2$-converter. The furnace gas contains CO and $CO_2$ which can be processed, in particular, in a biologically functioning further processing converter.

Preferably, the blast furnace comprises an aerosol inlet in a lower region of the blast furnace shaft above the surface of the molten metal bath, in particular, in the region of the blast-gas line. The aerosol can thus be fed as a reducing agent into the reduction zone of the blast furnace shaft. Moreover, when re-equipping an existing blast furnace so as to function in accord with the method being described here, at least a part of the already existing blast jets can be used as aerosol inlets.

The blast furnace advantageously comprises a plurality of aerosol inlets located at various heights of the blast furnace shaft. The aerosol can thus be directed into different regions of the blast furnace shaft, the process occurring in the different zones of the blast furnace shaft can be affected, and proper control of the process will be obtained.

Optionally, the aerosol inlets are partly located at a height which is below the surface of the molten bath in the blast furnace shaft when the blast furnace is operating. A reduction process can therefore be achieved in the molten metal bath when necessary.

Furthermore, the blast furnace optionally comprises a C inlet for carbon in the lowest region of the blast furnace shaft, this being arranged in such a way that carbon C can be introduced below the surface of the molten bath in the blast furnace shaft when the blast furnace is operational in order to lower the melting point of the metal. Optionally, this C inlet can be replaced or supplemented by the above-described optional aerosol inlet underneath the surface of the molten bath.

In one embodiment of the blast furnace, the $CO_2$-converter is adapted to reduce $CO_2$ to an aerosol in the presence of C-particles or a $H_2$/C-aerosol consisting of hydrogen and C-particles at a temperature of 800 to 1700° C. In these conditions, a region of the Boudouard equilibrium can be achieved, in which a high proportion of the introduced $CO_2$ is converted to CO. This embodiment is advantageous, if pre-heated carbon C or a $H_2$/C-aerosol is available, e.g. from a hydrocarbon converter.

Preferably, the blast furnace comprises a plasma or thermal energy operated hydrocarbon converter having at least one hydrocarbon inlet for a hydrocarbon-containing fluid and also at least one aerosol outlet for a $H_2$/C aerosol consisting of hydrogen $H_2$ and C-particles, wherein at least one of the aerosol outlets is connected to the $CO_2$-converter inlet. This embodiment is well suited for combination with a $CO_2$-converter which has a plurality of converter chambers and can directly process a hot $H_2/C$ aerosol. Hot carbon suitable for a process of reducing $CO_2$ taking place at high temperatures in the Boudouard equilibrium is thus made available from the furnace gas or exhaust gas of the combustion machine. Inert gases, e.g. argon or nitrogen are suitable as the plasma gas for example. On the other hand, hydrogen gas $H_2$, CO or synthesis gas also come into consideration since these gases result in any case during the decomposition of the hydrocarbons. The incoming hot hydrogen introduces additional heat energy into the $CO_2$-converter. Furthermore, the hydrogen can be introduced as a constituent of a $H_2/CO/C$ aerosol into the blast furnace shaft where it reduces the metal ore.

Preferably, the blast furnace comprises a plasma or thermal energy operated hydrocarbon converter having at least one hydrocarbon inlet for a hydrocarbon-containing fluid and also at least one C outlet for carbon and at least one $H_2$ outlet for hydrogen ($H_2$) wherein at least one of the C-outlets for carbon is connected to the $CO_2$-converter inlet. Thus hot carbon for reduction of the $CO_2$ in the Boudouard equilibrium is made available from the furnace gas or exhaust gas of the combustion machine.

Advantageously, at least one of the $H_2$ outlets for hydrogen $H_2$ of the hydrocarbon converter is connected to the further processing converter. Alternatively, one of the aerosol outlets for a $H_2/C$ aerosol consisting of hydrogen and C-particles is connected via an intermediate particle filter to the further processing converter. Thus, larger quantities of hydrogen are made available at the further processing converter, thereby enabling the biological conversion process to produce a large amount of ethanol and little or no $CO_2$.

If the blast furnace comprises a plurality of different further processing converters which can be operated simultaneously, the ensuing mass flows of furnace gas, exhaust gas, C, CO gas, $H_2$ gas, $CO_2$ gas can be optimally used.

Preferably, the blast furnace comprises an auxiliary heating device which is adapted to heat the blast furnace shaft and in particular, the reduction and/or smelting zones thereof. Due to the additional heating, the high temperatures that are required for the reduction of the metal ore and for melting the metal can be achieved in every operational situation. Hereby, the auxiliary heating device advantageously employs at least such heat as a) results from one of the combustion machines mentioned above and/or b) which ensues from a further processing converter which is implemented as a combustion machine or a CO converter, and/or c) which results from a plasma or thermal energy operated hydrocarbon converter such as was mentioned above. The auxiliary heating device can also be an induction device which directly heats the pig iron in the smelting zone. Thus, only energy is introduced into the magnetic components, i.e. into the metal which, after all, is to be produced in the blast furnace shaft.

In summary, it is pointed out that the blast furnace described here and the method for processing metal ore offer a plurality of advantages. Less or no coal or coke is needed. Consequently, there is significantly less or no resultant ash and therefore fewer or no additives are necessary. Thus, on the one hand, the costs for transport and purchasing can be reduced and improved quality of the raw metal can be achieved on the other. Furthermore, there are fewer or no resultant cinders. Cinders floating on the melted raw metal are not necessary here since a reducing protective atmosphere is present in the blast furnace shaft.

BRIEF DESCRIPTION OF THE DRAWINGS

The invention and further details and advantages thereof will be discussed in the following with reference to exemplary embodiments and with reference to the attached Figures.

FIG. 5 is a schematic illustration of a hydrocarbon converter which may be used in a blast furnace according to any of the described embodiments;

FIG. 6 is a schematic illustration of a $CO_2$-converter which can be used in a blast furnace according to any of the described embodiments;

DESCRIPTION

In the following specification, the terms top, bottom, right and left as well as similar terms relate to the orientations and arrangements shown in the Figures and are only meant for describing the embodiments. These terms may refer to preferred arrangements but are not meant to be limiting.

Figure 1:
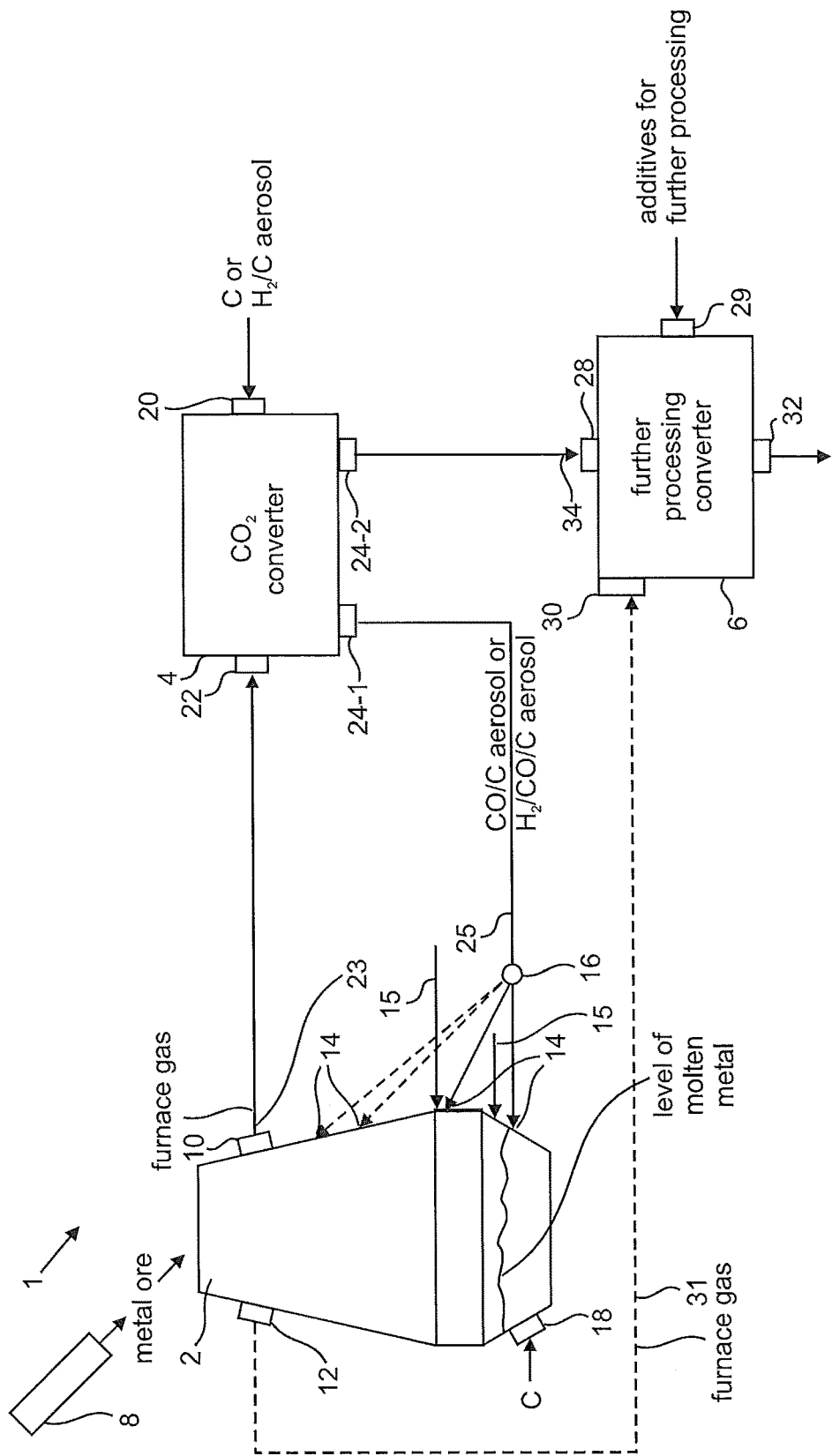
FIG. 1 is a schematic illustration of a blast furnace according to a first embodiment.

FIG. 1 shows a schematic illustration of a blast furnace 1 comprising a blast furnace shaft 2, a $CO_2$-converter 4 and a further processing converter 6. A feeder 8 is located at the upper end of the blast furnace shaft 2, wherein the feeder is adapted to feed raw material or feed stock into the blast furnace shaft 2. Specifically, the raw material is metal ore, and possibly necessary additives, reduction agents and combustible material for heating or initially heating the blast furnace.

Seen from top to bottom, the blast furnace shaft 2 comprises an inlet zone for a preheating process, a reduction zone, a carbonisation zone and a melting zone. In the inlet zone, the raw material is pre-heated. In the reduction zone, the metal ore, consisting primarily of metal oxide, is reduced to metal. In the carbonisation zone, there is formed a metal carbon mixture having a melting point of between 1000 and 1300° C. depending on the metal. In the melting zone, the metal carbon mixture (preferably an iron carbon mixture) is melted down by the combustion of heating material (e.g. coke, combustible gases, furnace gas etc.) or by means of an auxiliary heater. The raw metal collects at the bottom of the blast furnace shaft 2. During the process of smelting the metal ore, a gas mixture is formed in the blast furnace shaft 2. This gas mixture is referred to as furnace gas or flue gas. The furnace gas rises to the top of the blast furnace shaft 2 due to the low specific gravity thereof compared with that of the generally solid material and thereby conveys part of its thermal energy to the solid material.

In the classical blast furnace process, the furnace gas has a varying composition consisting of nitrogen ($N_2$, ca. 52-59%), carbon dioxide ($CO_2$, ca. 22-24%), carbon monoxide (CO, ca. 18-21%) and hydrogen ($H_2$, ca. 1-3%) and water vapour and possibly traces of methane ($CH_4$). The nitrogen and a portion of the oxygen emanate from the air being blown into the furnace shaft. Carbon dioxide, carbon monoxide and hydrogen are generated by chemical reactions during operation of the blast furnace, wherein these chemical reactions are well known to the skilled person and are not described in detail.

In the blast furnace process of the present disclosure, a larger amount of air could be blown into the blast furnace shaft 2 during the phase of preheating the blast furnace 1. However, as soon as stable operation of the blast furnace 1 is achieved, no appreciable amount of air is then blown into the blast furnace shaft 2. Since air is no longer entering the blast furnace shaft 2 from the outside, there is therefore no nitrogen and no oxygen inside the blast furnace shaft 2 when operating stably. Consequently, the furnace gas of the blast furnace process disclosed here contains virtually no nitrogen when operating stably. Rather, the furnace gas has a variable composition consisting of carbon dioxide ($CO_2$, ca. 50-53%), carbon monoxide (CO, ca. 42-46%) and hydrogen ($H_2$, ca. 2-6%) as well as water vapour ($H_2O$; depending on the residual humidity of the metal ore and the additives) and possibly traces of methane ($CH_4$). The gases $CO_2$ and CO are formed during chemical conversion of the ore. $CO_2$ and CO may also be formed from the additives. In practice, the ratio of CO to $CO_2$ in the furnace gas is variable and depends on the construction of the blast furnace, on the composition of the iron ore ($Fe_2O_3$ and/or $Fe_3O_4$), and on the process parameters etc.

It should be noted that in the blast furnace process of the present disclosure, comparably small amounts of air, and thus too, some oxygen and nitrogen may also enter the blast furnace shaft 2 due to leaks in the blast furnace shaft 2 or leaks in the supply lines or by means of auxiliary processes (e.g. by means of an auxiliary heater etc.). However, these amounts are very low and may be neglected for the blast furnace process of the present disclosure. Nitrogen is an inert gas and does not participate in any of the described chemical reactions. The amount of oxygen, which might result from a possibly minor amount of air entering the system, may be neglected when compared to the amount of oxygen which is already present in the metal ore (which is metal oxide). Consequently, these minor portions of gases will be neglected for the following description.

Both in the classical blast furnace process and in the blast furnace process of the present disclosure, dust particles and other pollutions are also contained in the furnace gas. These pollutions are filtered out by a dust catcher or filter so as to prevent pollution of other elements or components of the blast furnace. A dust catcher is well known to the skilled person and will not be described in detail.

Furthermore, it should be noted in this context that the described gases and gas components (CO gas, $CO_2$ gas, $H_2$ gas etc.) are, in fact, gas mixtures. In the following description, the gases will be named after their main constituent or their chemically active constituent so as to be better distinguishable. It will be obvious to the skilled person that the gases may also comprise admixtures or pollutants which do not have any effect upon the described process. In like manner, these gases may also contain chemically inactive components such as the nitrogen mentioned above. As an example, the CO gas according to the present description may consist of 90% carbon monoxide, but may also include up to 10% of other constituents. Carbon monoxide (CO) is combustible in the presence of oxygen. When, for example, a gas mixture comprising 90% carbon monoxide, 5% nitrogen and 5% $CO_2$ (such a mixture would be termed CO gas here) is burned, nitrogen and $CO_2$ would not participate in the oxidation reaction and would therefore be chemically inactive constituents.

A first furnace gas outlet 10 and an optional second furnace gas outlet 12 are located at the top of the blast furnace shaft 2. Different amounts of furnace gas may be exhausted from the furnace gas outlets 10, 12 during operation. Furthermore, a plurality of aerosol inlets 14 is provided at different heights of the blast furnace shaft 2. An aerosol consisting of (a) carbon monoxide and carbon (CO/C aerosol) or (b) an aerosol consisting of hydrogen, carbon monoxide and carbon ($H_2$/CO/C aerosol) may be blown into the blast furnace shaft 2 at different heights via the aerosol inlets 14. The type of aerosol being directed into the blast furnace shaft 2 depends on the type of $CO_2$-converter 4, i.e. a pipe $CO_2$-converter 4a or a filter $CO_2$-converter 4b. Furthermore, the type of aerosol introduced into the blast furnace shaft 2 also depends on whether C-particles or an aerosol consisting of hydrogen and carbon ($H_2$/C-aerosol) is introduced into the $CO_2$-converter 4. In particular, the following combinations (1) and (2) occur:

(1) The $CO_2$-converter 4 is a pipe $CO_2$-converter 4a comprising a converter chamber which is preferably tubular.

(1a) In operation, a molar excess of C-particles together with $CO_2$ is introduced into the pipe $CO_2$-converter 4a. Since there is not enough $CO_2$ gas available to convert all the C-particles into CO, there is a resultant CO/C-aerosol which emerges from the pipe $CO_2$-converter 4a. Here, the carrier gas for the emerging aerosol is CO.

(1b) If in operation a $H_2$/C-aerosol having a molar excess of C-particles together with $CO_2$ is introduced into the pipe $CO_2$-converter 4a, then a $H_2$/CO/C-aerosol emerges. Here, the carrier gas for the emerging aerosol is $H_2$/CO.

(2) The $CO_2$-converter 4 is a filter $CO_2$-converter 4b which comprises a plurality of converter chambers. In this case, when in operation, a $H_2$/C-aerosol ($H_2$ carrier gas and C-particles) is initially fed into a converter chamber in the filter $CO_2$-converter 4b and the $H_2$ carrier gas is separated from the C-particles. $CO_2$ gas is then introduced into the C-particle-filled converter chamber, wherein the $CO_2$ gas is introduced in molar excess compared with the C-particles. Since there is not enough $CO_2$ gas available to convert all the C-particles into CO, a resultant CO/C-aerosol is generated in the converter chamber.

Furthermore, a plurality of water inlets or $H_2O$ inlets 15 are provided in the blast furnace shaft 2 at different heights. Water $H_2O$ which is in the form of a vapour at the operating temperature of the blast furnace 1 can be fed through the $H_2O$ inlets 15. The $H_2O$ inlets 15 may be separate inlets from the aerosol inlets 14 (see FIG. 1) or the $H_2O$ inlets 15 may lead to the aerosol lines before the aerosol inlets 14 so that the water vapour $H_2O$ is mixed with the aerosol before being introduced into the blast furnace shaft 2 (see FIG. 2). As a further alternative, one subset of $H_2O$ inlets 15 could be separate from the aerosol inlets 14, and another subset of $H_2O$ inlets 15 may run together with the aerosol lines prior to the blast furnace shaft i.e. a combination of the two previously mentioned possibilities (see FIGS. 3 and 4).

In one embodiment that is not shown in the FIG., the $H_2O$ is introduced into the blast furnace shaft 2 together with the metal ore. The introduction of the $H_2O$ can be implemented by means of $H_2O$-inlets 15 located at the top of the blast furnace shaft 2, e.g. by means of an injection process, or via the feeder 8. One option for the introduction of the H$_2$O is damp metal ore which has not been previously dried before being fed-in via the feeder 8.

A distributor unit 16 is suitable for conveying one or more aerosol streams to the aerosol inlets 14 at different heights. The distributor unit 16 comprises for example a plurality of valves, flaps and pipes which are not shown in detail. At least one of the aerosol inlets 14 is located in a lower region of the blast furnace shaft 2 above the surface of the molten metal which is formed when the system is operating. In particular aerosol inlets 14 are provided in the region of the blasting-gas feed-lines in a known blast furnace shaft. In the event that an existing blast furnace is to be re-equipped so as to utilise the process being presented here, the existing blasting jets in the blast furnace shaft can be used as aerosol inlets 14. As a further option, at least one of the aerosol inlets 14 could be located at a height which is below the surface of the molten metal bath when the blast furnace 1 is operating.

A C-inlet 18 or an aerosol inlet 14 is arranged in the lower region of the blast furnace shaft 2. When the blast furnace is operational, carbon (C) can be introduced through the C-inlet 18 or the aerosol inlet 14 into the blast furnace shaft below the surface of the molten bath so as to reduce the melting point of the metal. As an alternative or in addition thereto, a C inlet 18 could be located in the region of the reduction zone, wherein powdered carbon is injected through this C inlet 18 so as to reduce the melting point of the previously reduced metal.

The CO$_2$-converter 4 may be any suitable CO$_2$-converter which can produce a H$_2$/CO/C aerosol or a CO/C aerosol. As mentioned above, the CO$_2$-converter 4 may be a pipe CO$_2$-converter 4a or a filter CO$_2$-converter 4b.

A pipe CO$_2$-converter 4a comprises a CO$_2$-converter inlet 20, a CO$_2$-converter gas inlet 22 and at least one aerosol outlet 24. The CO$_2$-converter 4 shown in FIG. 1 is depicted as being in the form of a pipe CO$_2$-converter 4a and comprises a first aerosol outlet 24-1 and a second aerosol outlet 24-2. The pipe CO$_2$-converter 4a comprises a converter chamber which is not shown in detail in FIG. 1 but which could in principle be of any shape. Preferably, the converter chamber is tubular since a tubular shape is stable and is easy to manufacture. Furthermore, tubular containers or chambers having various inlets and outlets in many configurations are readily obtainable commercially. The pipe CO$_2$-converter 4a is implemented in such a way that it can withstand the anticipated temperatures of 800 to 1700° C. when it is in operation. The CO$_2$-converter gas inlet 22 is directly connected by a first furnace gas connection 23 to the first furnace gas outlet 10 of the blast furnace shaft 2. Embodiments utilising indirect connections between the CO$_2$-converter gas inlet 22 and the furnace gas outlet 10 are also described later with reference to FIGS. 2 and 4.

In the following specification and in the claims, the terms "direct" and "indirect" and variations thereof, such as "directly connected" will be used. In this context the term "direct" means that a substance will be directed from one element of the blast furnace 1 to another element without any previous further processing. Accordingly, the term "indirect" means that a substance is routed from one element to another element wherein processing or conversion of the material is effected between said elements.

In the embodiment of FIG. 1, the pipe CO$_2$-converter 4a comprises a first aerosol outlet 24-1 and a second aerosol outlet 24-2. Alternatively, the pipe CO$_2$-converter could comprise just one aerosol outlet 24, wherein a divider that is not shown in the Figures is located downstream of said outlet 24, wherein said divider is able to route any desired portions of the aerosol flow produced in the CO$_2$-converter to different other converters or elements of the blast furnace 1. Furthermore, it is possible for the pipe CO$_2$-converter 4a to comprise a plurality of first aerosol outlets 24 which lead e.g. to a plurality of aerosol inlets 14 or to a plurality of divider units 16. Notwithstanding the above, the pipe CO$_2$-converter 4a may comprise a plurality of second aerosol outlets 26 which lead to different further processing converters 6.

The pipe CO$_2$-converter 4a operates according to a part reaction of a known reaction in a blast furnace, wherein said part reaction takes place at temperatures between 750° C. and 1200° C. without the necessity of a catalyst. Preferably, the pipe CO$_2$-converter 4a operates at a temperature between 800° C. and 1200° C. The operating temperature of the pipe CO$_2$-converter 4a may be chosen depending on the temperature of the introduced materials (i.e. furnace gas, CO$_2$-containing exhaust gas, carbon, aerosol). If the introduced materials have a high temperature, then the operating temperature of the pipe CO$_2$-converter 4a may also be high. As was discussed above, in the blast furnace process of the present disclosure, the furnace gas directed into the pipe CO$_2$-converter 4a primarily consists of carbon monoxide (CO) and carbon dioxide (CO$_2$). In the pipe CO$_2$-converter 4a, the CO$_2$ is directed over hot carbon (which may also be mixed with hydrogen) or is mixed therewith so as to be converted according to the following chemical reaction:

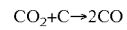

$$CO_2 + C \rightarrow 2CO$$

The carbon C introduced into the CO$_2$-converter 4 may simply be delivered from a storage tank. In the following description with respect to FIG. 4, an embodiment will be discussed wherein hot carbon C is produced and delivered by means of a hydrocarbon converter. The pipe CO$_2$-converter 4a operates best at the Boudouard-Equilibrium. At temperatures of 800° C., about 94% carbon monoxide will be delivered, and at temperatures of around 1000° C., about 99% carbon monoxide will be delivered. Herein, the CO$_2$ is added in molar excess compared with the carbon (C) in order to produce a CO/C aerosol. Furthermore, residual water may still be present as residual humidity in the metal ore and in the additives in the form of water vapour (H$_2$O) and will be converted in the pipe CO$_2$-converter according to the following reaction:

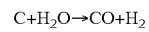

$$C + H_2O \rightarrow CO + H_2$$

The other components of the furnace gas (CO and possibly traces of N$_2$, H$_2$ and CH$_4$), which are also directed into the pipe CO$_2$-converter 4a, do not participate in the chemical conversion.

Figure 2:
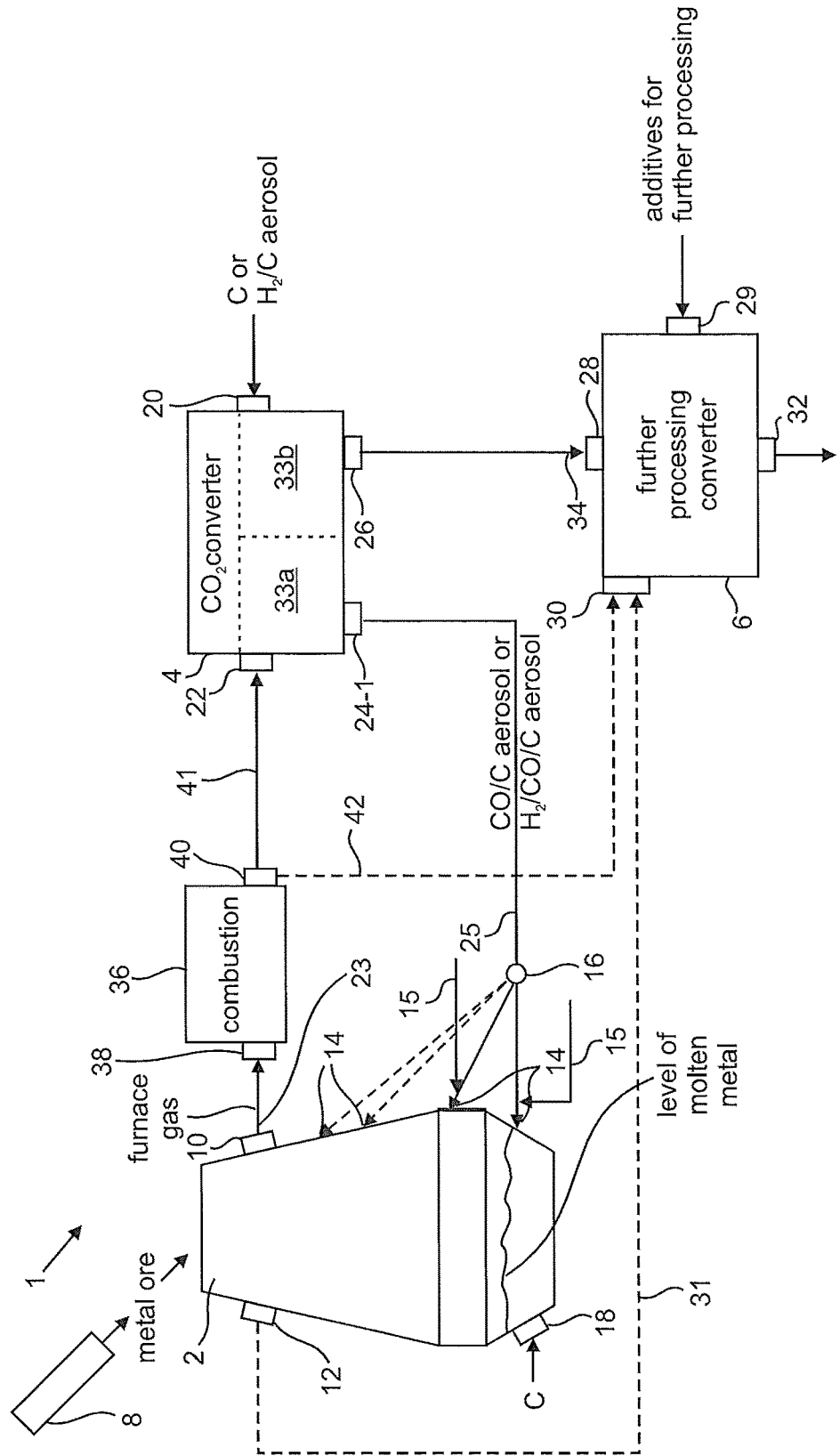
FIG. 2 is a schematic illustration of a blast furnace according to a second embodiment.

Consideration will now be given to an embodiment of the pipe CO$_2$-converter 4a that is shown in FIG. 2 and which comprises at least two converter chambers 33 that are depicted by broken lines. The converter chambers 33 are preferably tubular and arranged alongside one another in order to facilitate a thermal transfer process. The stream of C-particles or H$_2$/C-aerosol being fed into the pipe CO$_2$-converter 4a is distributed over the converter chambers 33. For the production of an aerosol in a first converter chamber 33a, a molar deficiency of CO$_2$ compared to the C-particles is added. In a second converter chamber 33b, the CO$_2$ and C-particles are introduced in molar equal quantities so that substantially only CO is produced. This CO is then passed on to the further processing converter 6 through a CO outlet 26.

In place of the pipe $CO_2$-converter 4a, a filter $CO_2$-converter 4b could also be used in all of the exemplary embodiments (FIGS. 1-4). Embodiments of the alternative filter $CO_2$-converter 4b are described with the aid of FIGS. 6 to 9. The filter $CO_2$-converter 4b comprises an $CO_2$-converter inlet 20, a converter gas inlet 22 as well as converter outlets 24, 26 and 27. Furthermore, the filter $CO_2$-converter 4b comprises two converter chambers 33, i.e. a first converter chamber 33a and a second converter chamber 33b. The converter chambers 33 each have a converter chamber inlet 35 for aerosol and a converter chamber inlet 37 for $CO_2$ gas.

The filter $CO_2$-converter 4b comprises at least two converter chambers 33. In the context of the converter chambers 33, the designations a, b, etc. are used for precise reference to the individual converter chambers 33. In a filter $CO_2$-converter 4b comprising four converter chambers 33, that would mean the designations a, b, c and d. The respective inlets, outlets, filters and other associated elements of the converter chambers 33 are likewise provided with the designations a, b, c, d etc. (e.g. filter 39a, 39b). Furthermore, the designations a, b etc. are used for the description of a switching scheme between the plurality of converter chambers 33 during the operation of the system (see below).

Furthermore, a respective filter 39 is arranged in the two converter chambers 33 (a filter 39a in the first converter chamber 33a and a filter 39b in the second converter chamber 33b). The filter 39 is suitable for filtering out particles from an aerosol being fed therethrough, here C-particles from the $H_2$/C-aerosol. In operation, a high temperature of several 100° Celsius, preferably of more than 850° C. prevails in the converter chambers 33 during the conversion of C and $CO_2$ to CO. The converter chambers 33 are therefore made from a heatproof material consisting of ceramic and/or metal for example. The filter 39 arranged in the converter chambers 33 is likewise made of a heatproof material. The filter 39 may be a wire filter or a ceramic filter for example. Likewise, the converter chambers 33 may comprise a porous ceramic base which serves as a filter 39. Thus, the filter 39 can be implemented separately from the housing of the converter chamber 33 or integrated therewith. The converter chambers 33 in FIG. 6 each have a converter chamber outlet 43 for hydrogen $H_2$ and a converter chamber outlet 44 for the respective output product which results from a conversion process in the filter $CO_2$-converter 4b. As mentioned above, the output product depends on the molar proportion of the introduced materials C and $CO_2$, a CO/C aerosol (when there is too little $CO_2$ for the conversion of the entirety of the C-particles) or a CO gas (when there is sufficient $CO_2$ for the conversion of the entirety of the C-particles) or a $CO_2$/CO gas (in the event of an excess of $CO_2$).

Herein, the expressions converter chamber inlet and converter chamber outlet are to be understood as guide means of any shape via which the above mentioned materials can be fed into the converter chamber 33 and removed from the converter chamber 33. A converter chamber inlet 35, 37 and a converter chamber outlet 43, 44 may, for example, comprise a long or short tube or hose line which opens out into the converter chamber 33, as well as valves, heating devices and cooling devices.

The converter chambers 33a, 33b can be filled with particles between a first (desired minimum) and a second (desired maximum) particle-filling level. It will be clear that the carbon-containing particles introduced with the $H_2$/C-aerosol will be caught in the filters 39 (39a, 39b in FIG. 6). A desired maximum particle-filling level is reached when there is a 70-90 percent loading of the filter by carbon-containing particles for example. The maximally desired particle-filling level can be established based on a drop of pressure in the converter chambers for example. A desired maximum particle-filling level is reached for example if the pressure drop in one of the converter chambers 33a, 33b is so large that satisfactory or economic operation of the filter $CO_2$-converter 4b is no longer ensured. When a desired maximum particle-filling level is reached in the left-hand (first) converter chamber 33a of FIG. 6, the introduction of a $H_2$/C-aerosol into the first converter chamber 33a is stopped and regeneration of this maximally filled left-hand (first) converter chamber 33a can begin by introducing $CO_2$. During the regeneration process, the particle-filling level of the regenerated converter chamber 33a decreases until a desired minimum particle-filling level is reached. The desired minimum particle-filling level here is a fixed particle-filling level which can be achieved after a reasonable regeneration period and adequate potential for the admission of new carbon-containing particles into the converter chamber 33 is ensured. The desired minimum particle-filling level may be 0%, but could also be a particle-filling level wherein the filters 39 are loaded to 5-15 percent with carbon-containing particles.

The filter $CO_2$-converter 4b comprises an aerosol diverting device 45 which is arranged between the $CO_2$-converter inlet 20 and the converter chambers 33 and is adapted to connect the $CO_2$-converter inlet 20 selectively to the first converter chamber 33a or to the second converter chamber 33b. Furthermore, the filter $CO_2$-converter 4b comprises a gas diverting device 47 which is arranged between the converter gas inlet 22 and the converter chambers 33 and is adapted to connect the converter gas inlet 22 selectively to the first converter chamber 33a or to the second converter chamber 33b. Alternatively, the aerosol diverting device 45 and the gas diverting device 47 can be implemented in the form of a single combined diverting device (not shown in FIG. 6), however separate implementation of the aerosol diverting device 45 and the gas diverting device 47 is advantageous since the aerosol and the gas have different flow and material properties and in operation they are at different temperatures. Furthermore, the filter $CO_2$-converter 4b comprises a lead-out device 49 which is arranged between the converter chambers 33 and the converter outlets 24, 26, 27 and is adapted to selectively connect the first converter chamber 33a or the second converter chamber 33b to the converter outlets 24, 26, 27 or to separate them therefrom.

Figure 3:
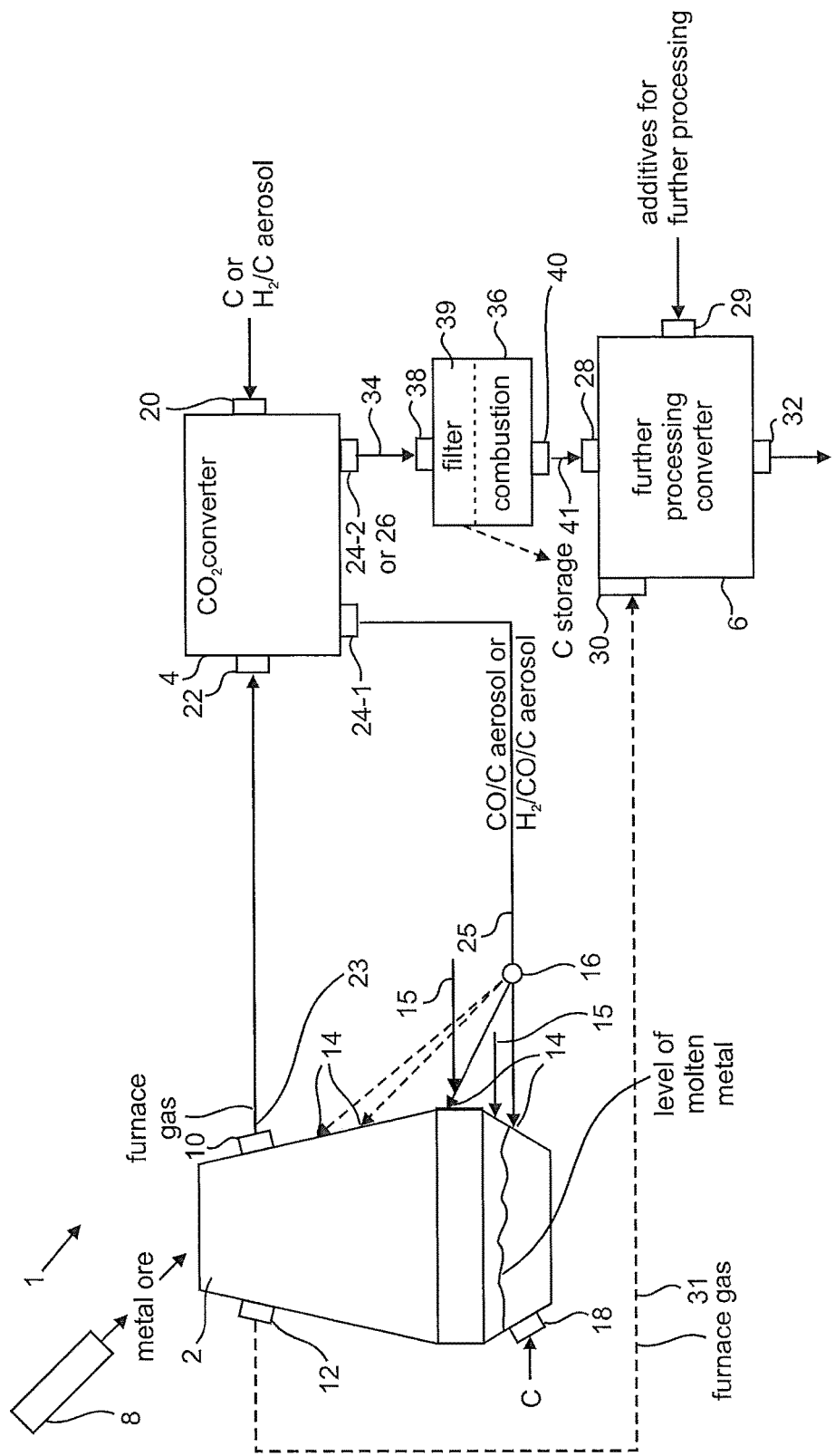
FIG. 3 is a schematic illustration of a blast furnace according to a third embodiment.

The $CO_2$-converter inlet 20 is connected to a supply source for a $H_2$/C-aerosol (not shown in FIGS. 1-3). The supply source for the $H_2$/C-aerosol can be a storage tank or an intermediate tank, or, the $H_2$/C-aerosol can be produced from hydrocarbon-containing fluids by a cracking process in a hydrocarbon converter (preferably a Kvaerner reactor, described hereinafter) which is operated by plasma or thermal energy. The $H_2$/C-aerosol has a high temperature due to the decomposition of hydrocarbon-containing fluids in a plasma or using thermal energy.

Figure 7:
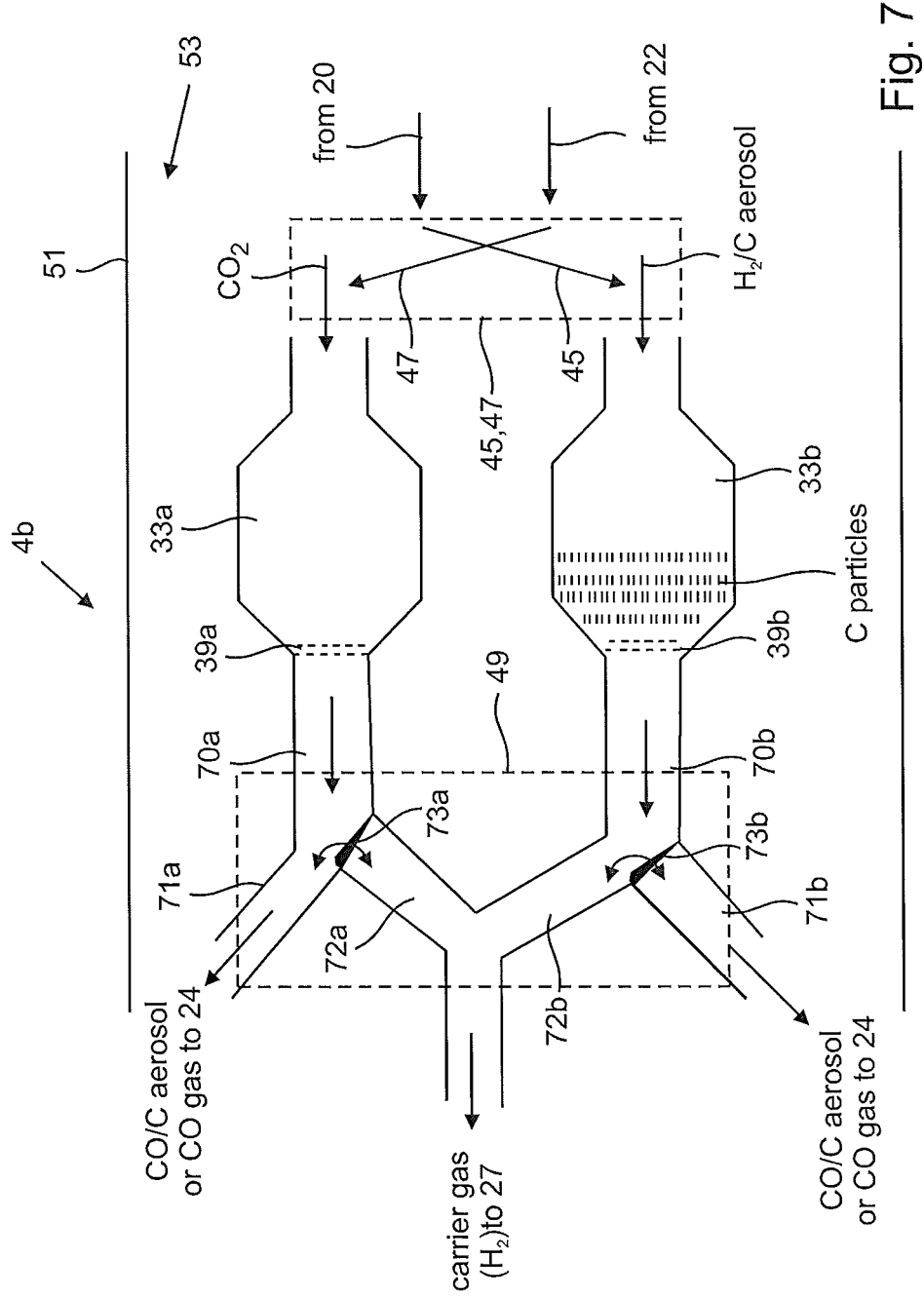
FIG. 7 is an illustration of the $CO_2$-converter shown in FIG. 6 with two converter chambers which comprises an aerosol diverting device, a gas diverting device and a lead-out device.

An example of an implementation of the lead-out device 49 which is suitable for both the aerosol diverting device 45 and the gas diverting device 47 is depicted on the left-hand side of FIG. 7. The lead-out device 49 comprises feed-in pipes 70a, 70b which are respectively connected to a converter chamber 33a or 33b. Furthermore, the lead-out device 49 comprises first branch pipes 71a, 71b and second branch pipes 72a, 72b which branch off from the respective feed-in pipes 70a, 70b. The branch pipes 71a, 71b, 72a, 72b can be connected to or separated from the associated feed-in pipe 70a or 70b by means of a closure element 73a or 73b. The closure elements 73a, 73b are implemented as flaps, as shown by arrows in FIG. 7, but they could also be in the form of displaceable blocking elements or valve plates. The closure elements 73a, 73b could also have any type of construction which would permit the feed-in pipe 70a or 70b to be connected to one of the branch pipes 71a, 71b, 72a, 72b or separated therefrom. In particular, the closure elements 73a, 73b are implemented in such a manner that only a few or no particle deposits can be deposited in the region of the transition between the feed-in pipe 70 and the branch pipes 71 or 72. In the position depicted in FIG. 7, a CO/C aerosol from the converter chamber 33a is introduced into the feed-in pipe 70a and fed upwardly to the left into the branch pipe 71a and then to the aerosol converter outlet 24. Moreover, the branch pipe 71b is closed by the closure element 73b in the position depicted in FIG. 7, and a $H_2$/C-aerosol which is introduced into and filtered in the converter chamber 33b would be fed from the feed-in pipe 70b via the branch pipe 72b to the carrier gas outlet 27.

Figure 8:
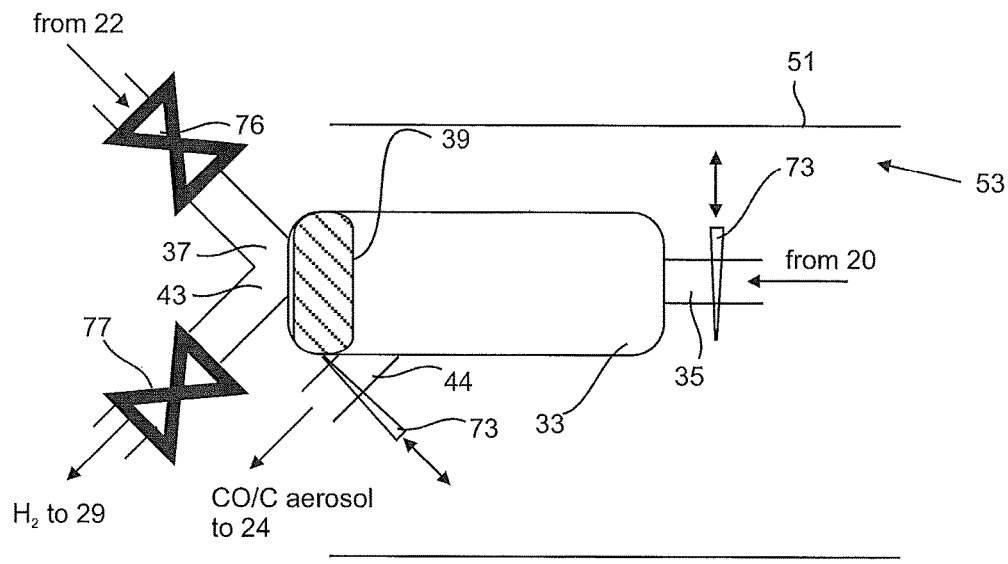
FIG. 8 is a schematic illustration of supply and discharge lines to a converter chamber of a $CO_2$-converter.

FIG. 8 shows an arrangement of the converter chamber inlets 35, 37 and the converter chamber outlets 43, 44 of a converter chamber 33. A $H_2$/C-aerosol can be introduced from the converter inlet 20 via the first converter chamber inlet 35. The introduction of the $H_2$/C-aerosol can be permitted or blocked by a closure element 73. A $CO_2$-containing gas can be introduced into the converter chamber 33 via a second converter chamber inlet 37. The introduction of the $CO_2$-containing gas can be controlled for example by a gas inlet valve 76 which provides the function of the closure element 73 here. The converter chamber 33 also comprises a first converter chamber outlet 43 which is arranged behind the filter 39 in the direction of flow of the $H_2$/C-aerosol. If a $H_2$/C-aerosol is introduced through the first converter chamber inlet 35, the filter 39 catches the carbon-containing particles from the $H_2$/C-aerosol. The $H_2$ carrier gas of the $H_2$/C-aerosol which is flowing through the filter 39 is derived via the first converter chamber outlet 43. The removal of the $H_2$ carrier gas can be permitted or prevented by a $H_2$ gas valve 77. In the embodiment of FIG. 8, the second converter chamber inlet 37 and the first converter chamber outlet 43 lie close together or coincide. Furthermore, the converter chamber 33 comprises a second converter chamber outlet 44 which is located before the filter 39 in the direction of flow of the $H_2$/C-aerosol. The second converter chamber outlet 44 can be closed or opened by a closure element 73 or by a gas valve which is not shown in FIG. 8.

The second converter chamber inlet 37 is arranged in such a way that a gas introduced therethrough in a direction of flow which is opposite to the direction of flow of the $H_2$/C-aerosol strikes the filter 39. In operation, the filter cake i.e. the carbon-containing C-particles picked up in the filter, can be stripped from the filter 39 by the injection of the $CO_2$-containing gas through the second converter chamber inlet 37 and thus better reactivity of the C-particles with the $CO_2$-containing gas can be ensured. A filled converter chamber can thus be regenerated more quickly, i.e. prepared for the introduction of a new filling of the $H_2$/C-aerosol.

Figure 9:
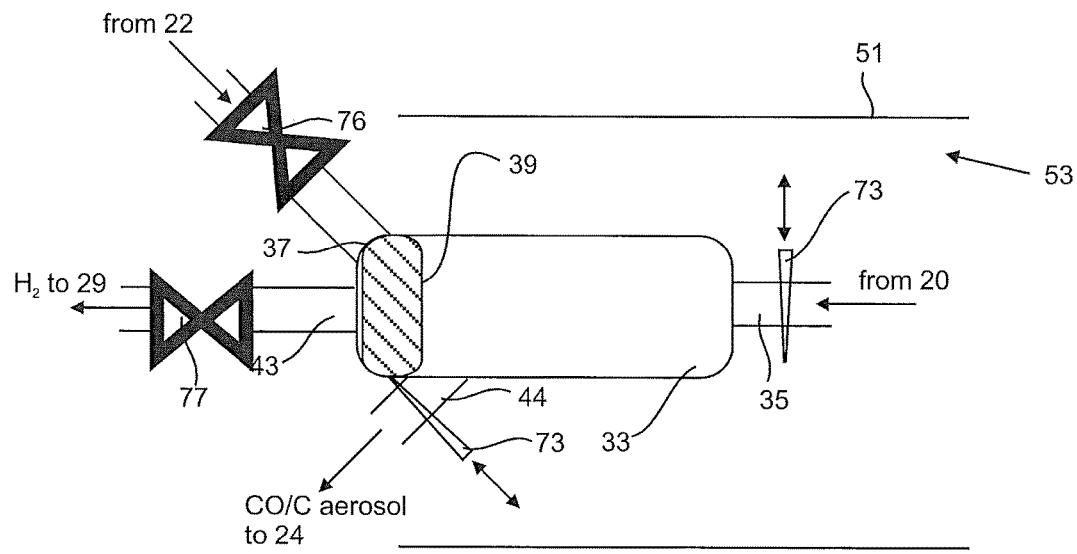
FIG. 9 is a schematic illustration of alternative supply and discharge lines to a converter chamber of a $CO_2$-converter.

FIG. 9 shows a similar arrangement of a converter chamber 33 with two converter chamber inlets 35 and 37 as well as two converter chamber outlets 43 and 44. In the embodiment of FIG. 9 and in contrast to FIG. 8, the second converter chamber inlet 37 and the first converter chamber outlet 43 do not spatially coincide. The construction of the embodiment of FIG. 9 is otherwise similar to that of FIG. 8.

Upon reaching the desired maximum particle-filling level of a converter chamber 33, i.e. after ending the supply of $H_2$/C-aerosol into the converter chamber 33, the $CO_2$-containing gas will blow against the direction of flow of the $H_2$/C-aerosol through the filter 39, whereby the carbon-containing C-particles arrested in the filter 39 will be released.

An optional guide sleeve 51 is arranged around the converter chambers 33 in both embodiments of the $CO_2$-converter 4 (the pipe and filter $CO_2$-converter 4a, 4b). The guide sleeve 51 can be formed from a metal sheet for example and it is substantially gas-tight. Two clearance spaces 53 are formed between the optional guide sleeve 51 and the converter chambers 33. The guide sleeve 51 has at least one gas supply inlet and at least one gas discharge outlet (not shown in the FIG.) through which, in operation, a fluid (especially $CO_2$-containing gas, liquid $H_2O$ or $H_2O$ vapour) can be introduced, guided through the clearance spaces 53 and then fed out. While a fluid is being guided through the clearance spaces 53 when the system is operating, the fluid absorbs heat which is being radiated by the converter chambers 33.

The converter gas inlet 22 is connected directly or indirectly to the furnace gas outlet 10. In the case of a direct connection (FIGS. 1 and 3), the converter gas inlet 22 receives a $CO_2$-containing furnace gas from the blast furnace shaft 2 when the system is operating. In the case of an indirect connection (FIGS. 2 and 4), the converter gas inlet 22 receives a $CO_2$-containing discharge gas (including pure $CO_2$) from the combustion machine 36 when the system is operating.

It will be clear for the skilled person that a $CO_2$-containing gas may also contain a larger proportion of constituents which do not participate in the reactions in the $CO_2$-converter 4 (see below), e.g. nitrogen or noble gases. Furthermore, the $CO_2$-containing gas could contain a small proportion of constituents (<5%) which can participate in the reactions in the $CO_2$-converter 4, but which are not detrimental to the functioning of the $CO_2$-converter 4 due to the small proportion thereof and thus have no appreciable effect on the conversion processes.

The further processing converter 6 is a device which is suitable for processing CO and $CO_2$ alone or in conjunction with other materials. In the simplest case, the further processing converter 6 is a furnace into which the aerosol (CO/C aerosol or $H_2$/CO/C aerosol) is introduced from the $CO_2$-converter 4. The inflammable components of the aerosol from the $CO_2$-converter 4 can be burned in such a furnace in order to provide an energy input in the form of additional heating for the blast furnace shaft 2, the $CO_2$-converter 4 or other sub-units of the blast furnace 1. In the following description, the case mainly being described is the one in which the further processing converter 6 processes a gas or a gas mixture. The solids in the aerosol from the $CO_2$-converter 4 can then be separated by an optional filter 39 which is arranged between the $CO_2$-converter 4 and the further processing converter 6 (see examples in FIGS. 3, 4a and 4b).

Alternatively, a $CO_2$-converter 4 with a plurality of converter chambers is used (a pipe or a filter $CO_2$-converter). The $CO_2$-converter 4 with a plurality of converter chambers is then operated in such a way that a portion of the externally-introduced $CO_2$ gas, furnace gas or exhaust gas is added in molar deficiency compared with the carbon material (C) in order to produce an aerosol which is directed into the blast furnace shaft 2. Another portion of the $CO_2$ gas, furnace gas or exhaust gas is brought into contact with the carbon and/or the C-particles in equal molar amounts so that CO develops from the $CO_2$ and substantially only gaseous material, mainly CO, emerges from the $CO_2$-converter 4. This CO is then passed on to the further processing converter 6. In every type of $CO_2$-converter comprising a plurality of converter chambers, the converter chambers preferably have a tubular shape and are arranged next to each in parallel other so as to form a bundle of tubes. The cross section of the tube is advantageously cylindrical, triangular, square or hexagonal in the longitudinal direction.

The further processing converter 6 comprises a further processing converter inlet 28, an additive inlet 29, an optional furnace gas inlet 30 and a further processing converter outlet 32. The further processing converter inlet 28 is connected via a connection line 34 to the aerosol outlet 24-2 (FIGS. 1 and 2) of the $CO_2$-converter 4. The optional furnace gas inlet 30 of the further processing converter 6 is connected to the second furnace gas outlet 12 of the blast furnace shaft 2 via a second furnace gas connection 31. In one simple embodiment, the further processing converter 6 may, for example, be a combustion machine which burns the supplied aerosol or combustible gas to form a $CO_2$-containing exhaust gas. If a particle filter (FIG. 4) and/or a combustion machine 36 (FIGS. 3 and 4) is arranged between the $CO_2$-converter 4 and the further processing converter 6, then the further processing converter 6 may be a bio converter or a CO converter which is able to produce synthetic functionalised and/or non-functionalised hydrocarbons. The possible implementations for the further processing converter 6 will be explained in the following and are applicable to all the embodiments:

A combustion machine which may be employed as one form of the further processing converter 6 may be e.g. a gas burner, a gas turbine or a gas engine. In the combustion machine, CO will be burned in the presence of oxygen or air (via the additive inlet 29) so as to produce energy for another machine and/or for generating heat. Furthermore, the further processing converter may be a fuel cell in which CO is oxidised with added oxygen. A combustion machine can be operated with a combustible CO/C aerosol or $H_2$/CO/C aerosol or a combustible gas from the $CO_2$-converter 4.

In a bio converter which is employed as an alternative form of further processing converter 6, a conversion process using microbes or algae is carried out according to one or more of the following net equations:

$$6CO+3H_2O \rightarrow C_2H_5OH+4CO_2; \quad \text{a)}$$

$$6H_2+2CO_2 \rightarrow C_2H_5OH+3H_2O; \quad \text{b)}$$

$$2CO+4H_2 \rightarrow C_2H_5OH+H_2O. \quad \text{c)}$$

In the case of a bio converter, naturally occurring or genetically modified microbes or algae are used for converting gases containing carbon monoxide (the furnace gas) or pure carbon monoxide (CO) coming from the $CO_2$-converter 4) or carbon dioxide which may be optionally mixed with hydrogen (as will be described below) into basic chemicals. Such basic chemicals are e.g. alcohol, ether or ester. In this conversion process, the key feature of these microbes or algae is used, i.e. the capability for they themselves to produce the hydrogen necessary for the reduction of carbon dioxide in a sort of internal Water-Shift reaction (WSR). The conversion of CO into ethanol ($C_2H_5OH$ or else $C_2H_6O$) may be summarised as follows:

$$6CO+3H_2O \rightarrow C_2H_5OH+4CO_2$$

If additional hydrogen is added, the following net reaction results:

$$6H_2+2CO_2 \rightarrow C_2H_5OH+3H_2O$$

Kerosene, diesel, gasoline, methanol or other fuels may also be produced if the appropriate microbes or algae are chosen. Suitable microbes or algae are known, e.g. anaerobic bacteria called *Clostridium* which are commercially available from the following companies: Coskata, USA, and BRI, USA, as well as Lanza Tech, New Zealand. In the bio converter, the microbes or algae are brought into contact with the introduced gases. In dependence on the type of microbes or algae, it should also be considered to feed additives supporting the vital functions of the microbes or algae into the bio converter. The construction and operation of a bio converter which is also known as a synthesis gas fermentation converter are known to the skilled person from the technical literature.

A third option for implementing the further processing converter 6 is a CO converter in which a synthesis gas is converted into a functionalised and/or non functionalised hydrocarbon, preferably into paraffin, kerosene, diesel, gasoline, liquid gases or methanol. In this case, the further processing converter 6 is e.g. a Fischer-Tropsch converter, a Bergius-Pier converter or a Pier converter. The construction and operation of such converters is known to the skilled person and will not be described in detail here. In the case where the further processing converter 6 is a CO converter, hydrogen is introduced via the additive inlet 29. This case will be described in more detail later with respect to FIG. 4.

A bio converter and a CO converter can be operated with gas (CO gas or $H_2$/CO gas mixture) from the $CO_2$-converter 4. If a CO/C aerosol or $H_2$/CO/C aerosol emerges from the $CO_2$-converter 4, then the solids can be separated from the carrier gas by means of an upstream particle filter. The remaining carrier gas (CO gas or $H_2$/CO gas mixture) can then be further processed in the bio converter or the CO converter.

Feeding the furnace gas from the blast furnace shaft 2 into the further processing converter 6 via the second furnace gas connection 31 is optional and is advantageous if the further processing converter 6 is a bio converter or a combustion machine.

Additives are introduced into the further processing converter 6 via the additive inlet 29, wherein the additives are necessary for further processing the CO or $CO_2$ in the further processing converter. These additives are e.g. hydrogen (in the case where the further processing converter 6 is a bio converter or CO converter), air or pure oxygen (in the case where the further processing converter 6 is a combustion machine), or other additives.

The further processing converter outlet 32 outputs the products produced by the further processing converter 6. This means that in the case of a gas engine or a gas turbine, the further processing converter outlet 32 is a motor shaft or a turbine shaft. In the case of a chemical further processing converter (bio converter or CO converter), the further processing converter outlet 32 is an outlet for chemical products produced in the further processing converter 6. In the case of a furnace, the further processing converter outlet 32 is an outlet for heat such as an outlet for hot water, water vapour, warm air or the like.

FIG. 2 shows another embodiment of the blast furnace 1 which is constructed in a similar way to the embodiment of FIG. 1. The same or corresponding elements of the blast furnace 1 that were already discussed with respect to FIG. 1 have the same reference signs in FIG. 2 and for the sake of brevity will not be discussed in detail here.

The blast furnace 1 shown in FIG. 2 additionally comprises a combustion machine 36 (i.e. additionally with respect to the blast furnace 1 of FIG. 1), wherein the combustion machine is located between the blast furnace shaft 2 and the $CO_2$-converter 4 (a pipe $CO_2$-converter 4a or a filter $CO_2$-converter 4b). The combustion machine 36 comprises a combustion gas inlet 38 and an exhaust gas outlet 40 for emitting an exhaust gas containing $CO_2$. The furnace gas outlet 10 of the blast furnace shaft 2 is connected to the combustion gas inlet 38. The exhaust gas outlet 40 is connected to the $CO_2$-converter gas inlet 22 of the $CO_2$-converter 4. This means that the first furnace gas outlet 10 is indirectly connected to the $CO_2$-converter gas inlet 22, since a combustion process takes place in the combustion machine 36 located between the blast furnace shaft 2 and the $CO_2$-converter 4.

The combustion machine 36 may be a gas engine, a gas turbine or a gas burner which produces exhaust gases containing $CO_2$. If the combustion machine 36 is a gas burner, the heat produced by the gas burner may be used for heating the blast furnace shaft 2 by means of an auxiliary heater or for preheating gases or other raw materials which are to be fed into the blast furnace shaft 2 or into the $CO_2$-converter 4. If the combustion machine 36 is a gas engine or a gas turbine, the outlet of the gas engine or gas turbine may be used for powering pumps or fans which may be necessary for the operation of the blast furnace 1.

As shown in FIG. 2, all of the exhaust gas containing $CO_2$ may be directed from the exhaust gas outlet 40 into the $CO_2$-converter 4 via a first exhaust gas connection 41 (as shown in solid lines). Optionally (as shown in dashed lines), a portion of the exhaust gas may be directed from the exhaust gas outlet 40 into the further processing converter 6 via a second exhaust gas connection 42, via the furnace gas inlet 30 for example.

FIG. 3 shows another embodiment of the blast furnace 1 which has a construction similar to the embodiments of FIGS. 1 and 2. The same or corresponding elements of the blast furnace 1 which have already been discussed with respect to FIG. 1 or 2, have the same reference signs and for the sake of brevity will not be discussed in detail here.

The blast furnace 1 shown in FIG. 3 additionally comprises a combustion machine 36 (i.e. additionally with respect to the blast furnace 1 of FIG. 1), wherein the combustion machine is located between the $CO_2$-converter 4 (a pipe $CO_2$-converter 4a or a filter $CO_2$-converter 4b) and the further processing converter 6. The combustion machine 36 comprises a combustion machine inlet 38 and an exhaust gas outlet 40 for discharging an exhaust gas containing $CO_2$. Apart from the aerosol outlet 24-1, the $CO_2$-converter 4 comprises a further aerosol outlet 24-2 or a CO outlet 26 which is connected to the combustion machine inlet 38. As explained above, the outlet of the $CO_2$-converter 4 depends on the molar ratio of C to $CO_2$ in the converter chambers 33, and thus the converter outlet shown to the right in the Figures has the function of being an aerosol outlet 24 or CO outlet 26, as indicted in the FIG. The exhaust gas outlet 40 is connected to the CO inlet 28 of the further processing converter 6. This means that the second aerosol outlet 24-2 or CO outlet 26 of the $CO_2$-converter 4 is only connected indirectly to the CO inlet 28 since a burning process takes place in the combustion machine 36 located between the $CO_2$-converter 4 and the further processing converter 6.

The combustion machine 36 may be a furnace, a gas engine, a gas turbine or a gas burner, which produces an exhaust gas containing $CO_2$. As mentioned above, either a CO gas (CO outlet 26) or an aerosol (aerosol outlet 24-2) emerge from the $CO_2$-converter 4. In the event that the combustion machine 36 cannot burn an aerosol (e.g. a gas engine, gas turbine or a gas burner), there is optionally provided at the combustion machine inlet 38 a filter 39 which is suitable for filtering out particles from the aerosol. The filter 39 can alternatively be arranged in the connection line 34. If the combustion machine 36 is a furnace or a gas burner, then the heat produced therein can be used in order to heat the blast furnace shaft 2 by means of an auxiliary heater or to preheat gases or other materials which are introduced into the blast furnace shaft 2 or into the $CO_2$-converter 4. If the combustion machine 36 is a gas engine or a gas turbine, the output of the gas engine or the gas turbine can be used for powering any sort of auxiliary machine such as pumps, induction coils or fans for example which are needed for operating the blast furnace 1.

Figure 4A:
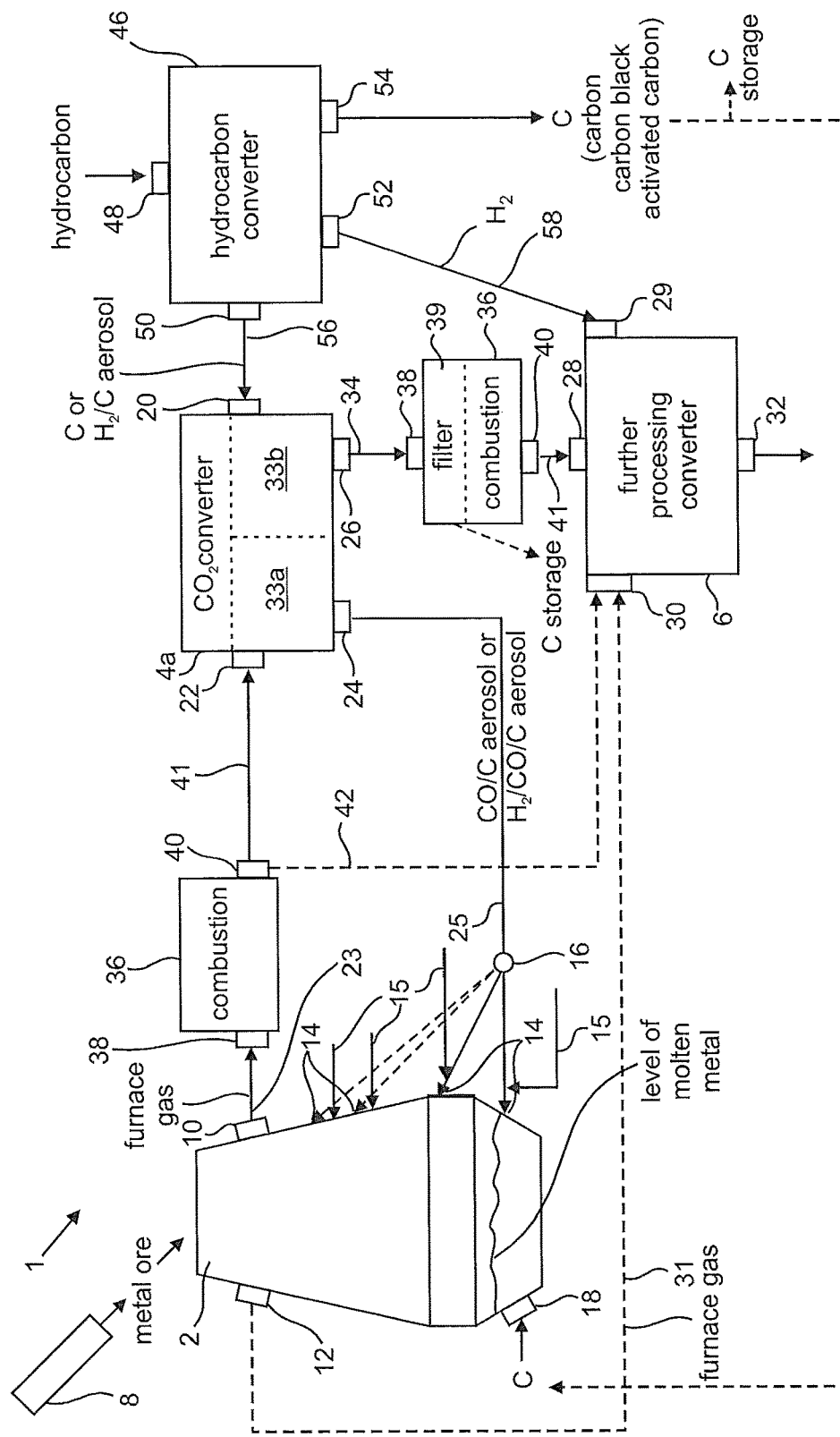
FIG. 4a is a schematic illustration of a blast furnace according to a fourth embodiment.

FIG. 4a shows another embodiment of the blast furnace 1 which has a construction similar to the embodiments of FIGS. 1, 2 and 3. The same or similar elements of the blast furnace 1 which have already been discussed with respect to FIGS. 1 to 3 have the same reference signs in FIG. 4a and for the sake of brevity will not be discussed again in detail here.

The blast furnace 1 shown in FIG. 4a comprises a combustion machine 36 which is located between the blast furnace shaft 2 and the $CO_2$-converter 4. The combustion machine 36 has already been described in detail with reference to FIG. 2. The introduction of the exhaust gases containing $CO_2$ from the exhaust gas outlet 40 is effected in the same way as was described above with respect to FIG. 2.

The blast furnace of FIG. 4a further comprises a hydrocarbon converter 46. The hydrocarbon converter 46 comprises at least one hydrocarbon inlet 48 for introducing a fluid containing hydrocarbons and also a first C outlet 50 for discharging at least carbon (optionally mixed with some hydrogen) and a $H_2$ outlet 52 for discharging hydrogen. The hydrocarbon converter 46 is any type of hydrocarbon converter which is able to convert or decompose hydrocarbons ($C_nH_m$) into carbon and hydrogen, particularly a hydrocarbon converter operated by means of a plasma or by means of thermal energy. The hydrocarbon converter 46 may optionally comprise a second C outlet 54 for discharging carbon. The first C outlet 50 is connected to the $CO_2$-converter inlet 20 of the $CO_2$-converter 4 via a C connection line 56. The $H_2$ outlet 52 is connected to the additive inlet 29 of the further processing converter 6 via a $H_2$ connection 58 and thus supplies $H_2$ as an additive. The first C outlet 50 and the $H_2$ outlet 52 may also be integrated into a combined outlet 50/52 for carbon and hydrogen. The combined outlet 50/52 is only shown in FIG. 4b, but may be present in all of the described embodiments. Carbon and hydrogen may be routed concurrently particularly in the form of a $H_2/C$ aerosol from the combined outlet 50/52 into the $CO_2$-converter 4.

The hydrocarbon converter 46 is preferably a plasma operated reactor, particularly a Kvaerner reactor. In the hydrocarbon converter, the hydrocarbons in the form of fluids containing hydrocarbon are decomposed at high temperatures by means of a plasma burner into pure carbon (for instance in the form of activated coal, carbon black, graphite or industrial soot) and hydrogen. Any suitable gas may be selected to serve as the plasma gas. Hydrogen gas $H_2$ is particularly suitable as it naturally occurs when decomposing hydrocarbons. The hydrocarbon-containing fluids used as starting material for the hydrocarbon converter 46 may be e.g. methane, natural gas, biogases, liquid gases or heavy oil. However, synthetic functionalised and/or non functionalised hydrocarbons may also be used as starting material for the hydrocarbon converter 46. In an alternative embodiment, the hydrocarbon converter 46 is operated with thermal energy and is able to decompose the hydrocarbons e.g. by means of pyrolysis. The process of decomposing the hydrocarbons should be done, if possible, in the absence of oxygen in order to suppress the undesirable formation of carbon oxides or water. Nevertheless, small amounts of oxygen which might be introduced together with the hydrocarbons are not detrimental to the process.

The hydrocarbon converter comprises a process chamber having an inlet for a fluid containing hydrocarbons, at least one unit for introducing decomposing energy into the fluid and at least one outlet. The decomposing energy is provided at least partially by heat which is generated by a plasma (plasma reactor) for example. Nevertheless, the decomposing energy may be also provided by other means (thermal reactor). Primarily, the decomposition process is carried out by heat. The fluid should be heated to a temperature above 1000° C. particularly above 1500° C. In the case of a plasma operated hydrocarbon converter, the plasma gas may be any suitable gas which is supplied from the exterior or is formed inside the hydrocarbon converter. Inert gases such as argon or nitrogen may be used as a plasma gas. Alternatively, gaseous hydrogen $H_2$ or gases produced during the process of decomposing the hydrocarbons would be an option.

The hydrocarbon converter 46 may be a high temperature reactor which works at a temperature of more than 1000° C. (e.g. a high temperature Kvaerner reactor). Alternatively, the hydrocarbon converter may be a low temperature reactor which works at a temperature of between 200° C. and 1000° C. (e.g. a low temperature Kvaerner reactor).

In another embodiment, the hydrocarbon converter 46 may be a combination of one or more high temperature reactors and one or more low temperature reactors. Such an arrangement will be described below in more detail with reference to FIG. 5.

The carbon produced in the hydrocarbon converter 46 may be discharged from the first C outlet 50 and the second C outlet 54 in varying proportions. The first C outlet 50 is used to direct a portion of the produced carbon (C-particles) into the $CO_2$-converter 4. The second C outlet 54 is used to extract a portion of the produced carbon that was not used in the $CO_2$-converter 4 for generating carbon monoxide. The carbon produced and the hydrogen have different temperatures depending on the construction of the hydrocarbon converter 46. The temperatures are between 200° C. and 1000° C. if a thermally operated reactor or a low temperature plasma reactor is used, however, the temperatures may be up to 1700° C. in the event that a high temperature plasma reactor is used. A variable portion of the hydrogen resulting from the decomposition process and emerging from the C outlet 50 may be fed into the $CO_2$-converter 4 together with the carbon. In this case, the C outlet 50 and the $H_2$ outlet 52 are combined (see e.g. FIG. 4b). The hydrogen is not detrimental to the above mentioned reaction of C and $CO_2$ in the $CO_2$-converter 4. The hydrogen may however function as a source of energy since it is very hot as a result of the decomposition process in the hydrocarbon converter 46.

As was mentioned above, the operating temperature of the $CO_2$-converter 4 may be chosen depending on the temperature of the raw materials being introduced (i.e. furnace gas, exhaust gas containing $CO_2$, carbon). If the carbon (and optionally the concurrently introduced hydrogen) directed into the $CO_2$-converter 4 has a high temperature of e.g. 1500° C. to 1700° C., then the operating temperature of the $CO_2$-converter 4 may also be high. If a hydrocarbon converter 46 is used which produces carbon having a temperature of only 200° C. to 700° C., then consideration should be given to the provision of additional heating for the $CO_2$-converter 4 so as to achieve a better $CO_2$ conversion of the furnace gas/exhaust gas at temperatures of >850° C. (see below). It should be noted that the temperature of the carbon depends not only upon the operating temperature of the hydrocarbon converter 46 but also on the construction of the connection line 56 (the length, insulation, etc.).

The carbon discharged from the second C outlet 54 may be removed from the process as an end-product such as activated coal, graphite, carbon black or other modifications such as carbon cones or carbon discs for example. Depending on the form and quality of the discharged carbon, the discharged carbon may be used as a raw material in the chemical industry or for the electronic industry. Conceivable applications are e.g. semiconductor production, tyre production, inks, toners or similar products. The carbon produced in the hydrocarbon converter 46 is a high purity raw material which may be easily further processed, particularly if a plasma operated hydrocarbon converter is used.

The optional second C outlet 54 of the hydrocarbon converter 46 may also be connected to the C inlet 18 of the blast furnace shaft 2 so that the carbon produced in the hydrocarbon converter 46 can be used in the blast furnace process.

In the embodiment of FIG. 4a, an additional combustion machine 36, as was described above with respect to the embodiment of FIG. 3, may optionally be provided between the $CO_2$-converter 4 and the further processing converter 6. The provision of a second combustion machine 36 between the $CO_2$-converter 4 and the further processing converter 6 depends on the further processing process planned for the further processing converter 6.

When the system is operational, a gas mixture emerges from the $CO_2$-converter 4 and this is processed in the further processing converter. In one case, this gas mixture is the carrier gas for an aerosol (CO or $H_2$/CO) emerging from the $CO_2$-converter 4. If the solids are separated from the aerosol, the carrier gas remains. In another case too, only a gas mixture can emerge if the $CO_2$-converter 4 is implemented in the form of a pipe $CO_2$-converter 4a or a filter $CO_2$-converter 4b with a plurality of converter chambers and the $CO_2$ and the C-particles are introduced in molar equilibrium in a part of the converter chambers. The gas mixture can be mixed with hydrogen from the hydrocarbon converter 46 to form a hydrogen-rich synthesis gas. The mixing process can take place directly in the further processing converter 6 or in a (not shown) upstream mixer.

The further processing converter 6 can thus be operated with a gas mixture comprising different proportions of $CO_2$, CO and $H_2$. The $CO_2$ proportion of the gas mixture directed into the further processing converter 6 comes from the exhaust gas of the combustion machine 36 in the case of the embodiment shown in FIG. 4a. The $CO_2$ proportion of the gas mixture is higher or lower depending on whether the combustion machines 36 are provided at all and in dependence on the amounts of furnace gas or CO the combustion machines 36 burn. The CO proportion of the gas mixture comes from the $CO_2$-converter, and the $H_2$ proportion comes from the hydrocarbon converter 46. The gas mixture may be called a synthesis gas. Synthesis gas, abbreviated as syngas, is a gas mixture of carbon monoxide and hydrogen which may also comprise carbon dioxide. Synthesis gas has about 50% of the energy content of natural gas. Synthesis gas can be burnt and may thus serve as a fuel source. Furthermore, the synthesis gas may also be used as an intermediate product for producing other chemical products.

The gas mixture fed into the further processing converter 6 is combustible and may generally be burnt so as to produce mechanical power or heating power. In this case, the further processing converter 6 is a combustion machine (a furnace or gas burner). The mechanical power produced therein may be used e.g. for producing electrical power or for powering other machines in the blast furnace 1. The ensuing combustion heat may be used e.g. for heating the blast furnace shaft 2.

The further processing converter 6 may also be a bio converter as was described above with respect to the embodiments of FIGS. 1 to 3. If the further processing converter 6 is a bio converter, it may be desired to direct varying proportions of CO and $CO_2$ into the further processing converter 6 depending on the type of microbes or algae being used therein. For example, a portion of the gas mixture may be directed directly into the further processing converter 6, while another portion of the gas mixture may be routed through a combustion machine 36 and may be burnt therein so as to produce heat and to provide more $CO_2$ to the further processing converter 6. Thus, a mixture of CO, $H_2$ and $CO_2$ may be delivered which is advantageous for the further processing converter 6. In the bio converter, the gas mixture is converted according to one of the above mentioned equations using algae or microbes in dependence on the proportions of $CO_2$, CO and $H_2$ in the gas mixture.

If the further processing converter 6 is a CO converter for producing functionalised and/or non-functionalised hydrocarbons, the gas mixture provided to the further processing converter 6 is a synthesis gas which mainly consists of CO and $H_2$. From said synthesis gas, the CO converter preferably produces paraffin, kerosene, diesel, gasoline, liquid gases or methanol by means of the above mentioned processes (Fischer-Tropsch process, Bergius-Pier process etc.). In this case, the gas mixture contains little or no $CO_2$-containing exhaust gas since CO and $H_2$ are preferably directed into the further processing converter 6.

Figure 4B:
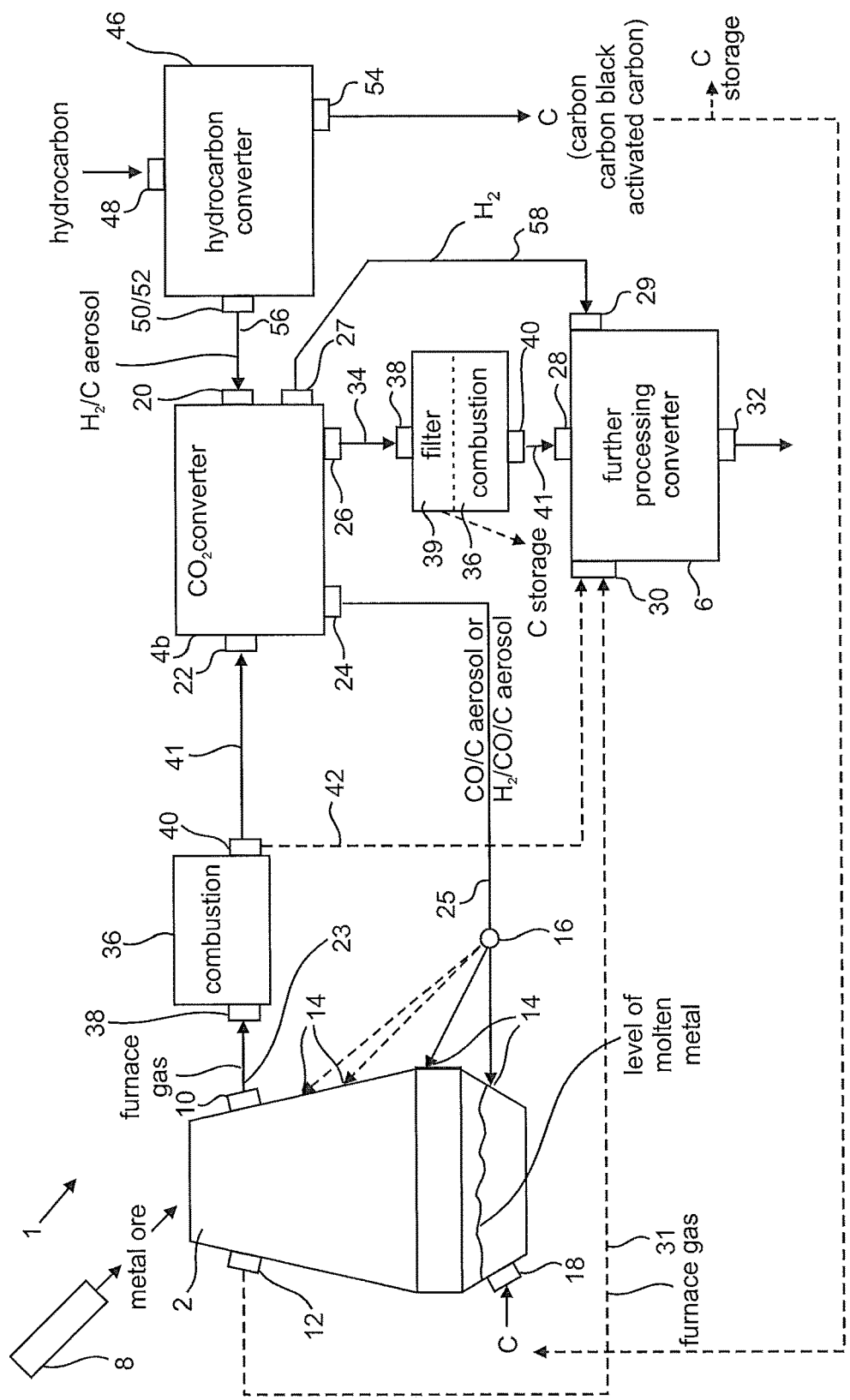
FIG. 4b is a schematic illustration of a blast furnace according to a fifth embodiment.

The blast furnace 1 shown in FIG. 4b is constructed in substantially exactly the same manner as the blast furnace shown in FIG. 4a. However the arrangement of the converters 4, 6 and 46 differs as follows. The hydrocarbon converter 46 comprises a combination outlet 50/52 for $H_2$ gas and C-particles, i.e. for a $H_2$/C-aerosol. The combined outlet 50/52 is connected to the $CO_2$-converter inlet 20. The $CO_2$-converter 4 is a filter $CO_2$-converter 4b which comprises three converter outlets i.e. an aerosol outlet 24, a CO outlet 26 and a carrier gas outlet 27. The aerosol outlet 24 is connected to the blast furnace shaft 2, the CO outlet 26 is connected via the combustion machine 36 to the further processing converter 6 and the carrier gas outlet 27 is connected to the additive inlet 29 of the further processing converter 6.

In the case of all the embodiments mentioned above, it should be noted that the furnace gas which is fed from the optional second furnace gas outlet 12 and through the optional second furnace gas connection 31 may be purified from harmful materials such as sulphur, ash, heavy metals and other substances which might be detrimental to the corresponding further processing converter 6. In one case where the further processing converter 6 is just a simple combustion machine however, non-purified furnace gas from the second furnace gas outlet 12 may also be used.

For all the embodiments mentioned above, it should further be noted that a portion of the $CO_2$-containing exhaust gas from one of the combustion machines 36 may be routed directly to the further processing converter 6 if a particular $CO_2$ proportion is desired for the further processing converter 6.

In all the exemplary embodiments in FIGS. 1 to 4, provision may be made for an auxiliary heating device which is not shown in the Figures but is suitable for heating the reduction zone in the blast furnace shaft 2. This auxiliary heating may possibly be necessary because, in comparison with the conventional blast furnace process in which the coke or coal and iron ore are fed into the blast furnace shaft 2 with additional materials, lower processing temperatures are to be expected. Thus, it may be necessary to provide additional heating depending upon the construction and the size of the blast furnace shaft 2 and dependent on the temperature of the flows of material into the blast furnace shaft 2. This auxiliary heating device can employ the heat which arises from one of the combustion machines 36 or which arises in the further processing converter 6 if this is a combustion machine. Furthermore, it should be considered that the auxiliary heating device uses waste heat from the hydrocarbon converter 46. That is to say that the hydrocarbon converter 46 produces a considerable amount of waste heat in the hydrocarbon decomposing process regardless of whether the hydrocarbon converter 46 is functioning thermally or with a plasma. Moreover, induction heating could also be considered, such a process directly heating the raw metal in the blast furnace shaft 2 that is to be melted.

Furthermore, it should be mentioned that in all the exemplary embodiments of FIGS. 1 to 4, more than one $CO_2$-converter, more than one hydrocarbon converter, more than one combustion machine and more than one further processing converter all of which operate in parallel can be provided depending upon the size of the various converters and the blast furnace shaft 2.

Likewise for all the exemplary embodiments of FIGS. 1 to 4, it should be taken into account that a plurality of further processing converter 6 are used which work according to different principles. For example, a first converter 6 can be implemented as a gas burner (first combustion machine) for the additional heating of the blast furnace shaft, a second further processing converter 6 which is operated in parallel with the first further processing converter can be implemented as a gas turbine (second combustion machine), wherein the gas turbine is used in order to operate pumps or fans and if necessary the induction coils of an induction heating system for the blast furnace 1, a third further processing converter 6 which likewise operates in parallel can be operated with a synthesis gas consisting of CO and $H_2$ (CO converters of the Fischer-Tropsch type etc.) in order to produce hydrocarbons as described above, and the remaining gas mixture can be broken down in a fourth further processing converter 6 using a biological process employing algae or microbes (bio converter). A bio-converter can also be operated in parallel with a Bergius-Pier or Fischer-Tropsch converter.

In all the exemplary embodiments of FIGS. 1 to 4, the $CO_2$-converter 4 can be implemented as a pipe $CO_2$-converter 4a with a plurality of converter chambers, or as a filter $CO_2$-converter 4b. All the embodiments of the further processing converter 6 can be used in the exemplary embodiments of FIGS. 1 to 4. Likewise, all the combinations of the $CO_2$-converters 4 and the further processing converters 6 can be used together. Filters or separators are used as necessary in the event that a converter cannot process a material, e.g. a particle filter prior to a bio-converter or CO converter.

Based on the discussion above, the following advantageous combinations may be summarized:
1. A $CO_2$-converter 4, which reduces $CO_2$ in the presence of a molar excess of C according to the Bouduoard equilibrium, combined with a further processing converter 6 which is a combustion machine, a bio converter or a CO converter running with synthesis gas.
2. A $CO_2$-converter 4, which reduces $CO_2$ and a $H_2$/C aerosol to a $H_2$/CO/C aerosol in the presence of a molar excess of C according to the Bouduoard equilibrium, combined with a further processing converter 6 which is a combustion machine, a bio converter or a CO converter running with synthesis gas.
3. A $CO_2$-converter 4 with a plurality of converter chambers in which, in operation, the proportion of $CO_2$ and C in a converter chamber is regulated in such a way that a $H_2$/CO/C aerosol or a CO/C aerosol develops according to the Bouduoard equilibrium and a CO gas or a $H_2$/CO gas without C-particles develops in another converter chamber which is introduced into a further processing converter 6 which is a combustion machine, a bio converter or a CO converter running with synthesis gas.

A bio converter and a CO converter running with synthesis gas are particularly advantageous further processing converters 6 since little or no $CO_2$ escapes from the total process with these variants.

In all the embodiments mentioned above, it is advantageous if the carbon necessary for reducing $CO_2$ is produced in a hydrocarbon converter which may be operated with readily available and low cost hydrocarbons. Particular consideration is given to the fact that naturally occurring gases containing hydrocarbons, i.e. natural gas, fracking gas or other readily available and low cost gases can be fed into the hydrocarbon converter 46.

The operation of the exemplary embodiments of FIGS. 1 to 4 is described hereinafter. First, the basic operation will be explained based on the simple illustration of the first exemplary embodiment.

In operation, metal ore, mainly consisting of metal oxides, is fed into the blast furnace shaft via the feeder 8. In operation, there is a temperature distribution in the blast furnace shaft 2 from the top to the bottom ranging from about 200 to 2000° C. Thus, the drying and preheating zone has a temperature of about 200° C., a temperature of about 400 to 900° C. prevails in the reduction zone, a temperature of about 1000 to 1500° C. prevails in the carbonisation zone, and a temperature of about 1200 to 1800° C. prevails in the melting zone.

As mentioned above, the raw materials fed-in via the feeder 8 are usually metal ore, additives and coke or coal serving as heating and reducing means. By means of the process according to the present disclosure, the process of feeding-in coke or coal as a heating and reducing means may be reduced or even totally omitted when the system is running stably. It is only in the beginning of the operation that it may be necessary to feed-in large amounts of coke or coal as a heating material. When operating stably and continuously, reduction of the metal ore and particularly reduction of metal oxides is finally achieved by means of a $H_2$/CO/C aerosol or a CO/C aerosol which is directed into the blast furnace shaft 2 together with $H_2O$. In the blast furnace process being described here, the composition of the furnace gas mentioned above is only expected at the beginning of the operation since a still larger quantity air can be blown into the blast furnace shaft 2 during the process of heating up the blast furnace 1.

As soon as stable operation of the blast furnace 1 is achieved and stable temperatures have set in, no substantial amount of air is blown into the blast furnace shaft 2. The furnace gas of the blast furnace process of the present application thus contains no nitrogen when operating stably, but rather, it consists of a variable mixture consisting of carbon dioxide ($CO_2$, about 50-53%), carbon monoxide (CO, about 42-46%) and hydrogen ($H_2$, about 2-6% dependent on whether a $H_2$/CO/C aerosol or a CO/C aerosol is fed into the blast furnace shaft) as well as water vapour ($H_2O$; depending on the humidity of the ore and optional additives) and possibly traces of methane ($CH_4$).

The furnace gas is hot and light and thus rises in the blast furnace shaft 2 when the system is operating. The rising furnace gas is discharged out of the first furnace gas outlet 10 and fed into the $CO_2$-converter 4 via the first furnace gas connection 23.

For the purposes of operating the $CO_2$-converter 4, the combinations which were described above are used i.e. (1a) introduction of C-particles into a pipe $CO_2$-converter 4a, (1b) introduction of a $H_2$/C-aerosol into a pipe $CO_2$-converter 4a and (2) introduction of a $H_2$/C-aerosol into a filter $CO_2$-converter 4b, the functioning of which are follows.

(1a) If the $CO_2$-converter 4 is a pipe $CO_2$-converter 4a and this is supplied with hot C-particles, the carbon (C-particle) is introduced via the $CO_2$-converter inlet 20 into the pipe $CO_2$-converter 4a. The carbon may simply come from a C-storage tank according to FIG. 1. Alternatively, the carbon comes from the hydrocarbon converter 46 and already has a high temperature when entering the pipe $CO_2$-converter 4a, as will be described later. The carbon is optionally mixed with hydrogen ($H_2$/C-aerosol).

Furnace gas which mainly contains $CO_2$ is introduced into the pipe $CO_2$-converter 4a via the $CO_2$-converter gas inlet 22 and fed over the hot carbon C or is mixed with the $H_2$/C-aerosol. As mentioned above, when the present process is operating stably, the furnace gas consists mainly of $CO_2$ and CO in variable proportions and it has a temperature of 250 to 400° C. in the blast furnace process. The hot carbon is delivered via the $CO_2$-converter inlet 20 to the pipe $CO_2$-converter 4a. The pipe $CO_2$-converter 4a works at the Boudouard equilibrium which sets in during the conversion of carbon dioxide with hot carbon. The "Boudouard reaction" is known to the skilled person and will not be described in detail here:

$$CO_2 + C \rightarrow 2CO \quad \Delta H = +172.45 \text{ kJ/mol}$$

As mentioned above, a conversion of possibly existing water vapour ($H_2O$) also takes place, in the pipe $CO_2$-converter 4a to a small extent in accord with the equation:

$$H_2O + C \rightarrow CO + H_2 \quad \Delta H = +131.4 \text{ kJ/mol}$$

The above mentioned variable proportion of CO to $CO_2$ in the furnace gas is taken into account by controlling the reaction occurring in the pipe $CO_2$-converter 4a. The just described reactions are effected without catalyst.

If the pipe $CO_2$-converter 4a has only one converter chamber (e.g. as shown in FIG. 1), a smaller molar quantity of $CO_2$ with respect to the available C is introduced into the converter chamber of the pipe $CO_2$-converter 4a in order to produce a CO/C aerosol. In this case, the thus produced CO/C aerosol emerges through the aerosol outlets 24-1 and 24-2.

If the pipe $CO_2$-converter 4a has a plurality of converter chambers 33 (e.g. two converter chambers 33a and 33b, as shown in FIG. 2), then as much carbon (C) as is necessary for the conversion of the carbon dioxide and the water vapour is introduced into the converter chamber 33 of the pipe $CO_2$-converter 4a so that CO gas is produced. However a smaller molar quantity of $CO_2$ present as C is introduced into another converter chamber 33 of the pipe $CO_2$-converter 4a in order to produce a CO/C aerosol. The thus produced CO/C aerosol emerges in this case through the aerosol outlet 24-1 and is fed via the aerosol connection 25 to the blast furnace shaft 2. The thus produced CO gas emerges from the CO outlet 26 (instead of an aerosol outlet 24-2) and is fed to the further processing converter 6.

Furthermore, the temperature in the pipe $CO_2$-converter 4a is regulated in such a way as to obtain the best possible degree of conversion. At temperatures of 800° C., about 94% carbon monoxide is delivered, and at temperatures of around 1000° C. about 99% carbon monoxide is delivered. In an ideal case, the carbon dioxide ($CO_2$) in the $CO_2$-converter 4 is thus almost completely converted with the carbon (C) being supplied and there ensues (almost 99%) CO gas or a CO/C aerosol which only contains negligible quantities of $CO_2$. Averaged over time, the quantity of gas in the circuit between the blast furnace shaft 2 and the pipe $CO_2$-converter 4a is then doubled due to the supply of carbon via the $CO_2$-converter inlet 20. Consequently, in this case, half of the substance (CO gas or CO/C aerosol) produced from the furnace gas being treated is exhausted from the pipe $CO_2$-converter 4a elsewhere, namely, via the second aerosol outlet 24-2 or via the CO outlet 26 into the further processing converter 6.

A hot gas mixture or CO/C aerosol consisting almost entirely of carbon monoxide (CO) or CO/C at a temperature of about 800° C. to 1000° C. (depending on the operating temperature of the pipe $CO_2$-converter 4a) emerges from the pipe $CO_2$-converter 4a. The conversion rate depends on the process control system (control of pressure and temperature) as mentioned above. For the purposes of simplification here, the gas mixture or the aerosol exiting from the $CO_2$-converter will be referred to respectively as carbon monoxide or CO gas and CO/C aerosol. The CO gas exiting from the $CO_2$-converter 4 also contains heat energy which can be used directly or indirectly via a heat exchanger not shown in FIG. 1, e.g. for preheating the furnace gas having a high $CO_2$ content that is being directed into the $CO_2$-converter gas inlet 22.

(1b) If the $CO_2$-converter 4 is a pipe $CO_2$-converter 4a and this is supplied with a hot $H_2$/C-aerosol, the $H_2$/C-aerosol is directed into the pipe $CO_2$-converter 4a via the $CO_2$-converter inlet 20. According to FIG. 1, the carbon can simply come from a $H_2$/C-aerosol temporary storage facility or a $H_2$/C-aerosol storage tank. Alternatively, as described with reference to the exemplary embodiment of FIG. 4, the $H_2$/C-aerosol comes from the hydrocarbon material converter 46 and is already at a high temperature when entering the pipe $CO_2$-converter 4a, as will be described later.

The modus operandi for the version (1b) is the same as was described above for version (1a). The difference is that a portion of the hydrogen $H_2$ also goes through the pipe $CO_2$-converter 4a. The hydrogen $H_2$ does not however participate in the above described Boudouard reaction. Consequently, a $H_2$/CO/C aerosol emerges from the pipe $CO_2$-converter 4a if a molar surplus of C-particles is present. If a pipe $CO_2$-converter 4a with a plurality of converter chambers is provided, a molar equilibrium of C-particles and $CO_2$ can be maintained in a part of the converter chambers. A $H_2$/CO gas mixture (synthesis gas) will then emerge from the converter chambers with molar equilibrium. In the other part of the converter chambers, a surplus of C-particles compared with the $CO_2$ is supplied in order to produce a $H_2$/CO/C aerosol, i.e. the carrier gas of the $H_2$/CO/C aerosol comprises a portion of $H_2$.

(2) The $CO_2$-converter 4 is a filter $CO_2$-converter 4b with a plurality of converter chambers (FIGS. 6-9). In operation, a $H_2$/C-aerosol is initially directed into a converter chamber and the $H_2$ carrier gas is separated from the C-particles. $CO_2$ gas is then introduced into the converter chamber filled with C-particles, wherein the $CO_2$ gas is introduced in a molar deficiency in relation to the C-particles. Since there is an insufficiency of $CO_2$ gas to convert all the C-particles into CO, an CO/C aerosol thus ensues. At the same time, another converter chamber is supplied with a $H_2$/C-aerosol.

As described above for versions (1a) and (1b), the output of the filter $CO_2$-converter 4b is a CO/C aerosol according to the Boudouard conversion when it is supplied with a molar deficiency of carbon dioxide (if necessary with an inert or slightly (<5%) reactive admixture). The Boudouard conversion takes place in the converter chambers 33a, 33b alternately, as will be described in more detail below.

The aerosol diverting device 45 and the gas diverting device 47 switch back and forth between delivery of a $H_2$/C-aerosol or $CO_2$ to the first and second converter chambers 33a and 33b dependent on the level to which the converter chambers 33 are filled with C-particles. The lead-out device 49 connects a converter chamber 33a, 33b to the converter outlet 27 for the carrier gas $H_2$ if the respective converter chamber 33a, 33b is supplied with a $H_2$/C-aerosol, and to the converter outlet 24 for CO/C aerosol if the respective converter chamber 33a, 33b was previously filled with C-particles and $CO_2$-containing exhaust gas or furnace gas is now being delivered so that a CO/C aerosol forms. This will be explained again in more detail below in connection with the operation of the blast furnace according to FIG. 4b.

In all of the embodiments, the CO/C aerosol or the $H_2$/CO/C aerosol is fed from the $CO_2$-converter 4 via the aerosol connection 25 to the aerosol inlets 14 in the blast furnace shaft 2 when the system is in operation. Differing quantities of the aerosol can be introduced into the blast furnace shaft 2 at different heights by means of the distributor unit 16. As soon as the aerosol enters the blast furnace shaft 2, CO and nascent (self-forming) hydrogen H develops therein in the presence of the metallic oxide and the water vapour which is introduced through the $H_2O$-inlets 15. This self-forming or atomic hydrogen is substantially more reactive than the usual molecular hydrogen $H_2$. The nascent hydrogen reduces Fe(III) to Fe(II) (according to the equation: $Fe_2O_3 + 2H \rightarrow 2FeO + H_2O$), and the CO then reduces the Fe(II) to iron Fe. Thereby, the reduction from Fe(III) to Fe(II) is faster than the corresponding reduction with CO. Water $H_2O$ and $CO_2$ is thereby formed again. Further $CO_2$ (from aggregates) and water (from the aggregates and from the ore) is produced from the aggregates and the metal ore. The CO gas and the nascent hydrogen (H) thus work in the blast furnace shaft 2 as reducing agents and reduce the metallic oxide. The aerosol should be considerably hotter than 1000° C. for two reasons: a) energy supply to the blast furnace and b) a shift of the Boudouard equilibrium in the blast furnace shaft 2 on the part of the CO.

Only a little water is needed when operating the blast furnace shaft 2 described above because water and hydrogen are subsequently delivered interdependently. It is preferred that 0.1 to 10% water vapour in proportion to the aerosol be introduced, and especially preferred is 0.1 to 1% water vapour. The total quantity of hydrogen available in the blast furnace shaft 2 results from the quantity of carbon in the aerosol. The process is controlled in such a way that, if possible, no $CO_2$ will enter the blast furnace shaft 2 as otherwise the Boudouard reaction ($C+CO_2 \rightarrow 2CO$) would arise in the presence of the carbon particles in the aerosol. The Boudouard reaction is strongly endothermic and would extract a lot of heat energy from the blast furnace shaft 2. Since the Boudouard reaction should be suppressed insofar as possible no more carbon than is necessary for the generation of the hydrogen should be added if at all possible.

Because in stable operation of the present blast furnace process no new nitrogen is supplied from the air, the proportion of nitrogen reduces after a period of operation of the blast furnace 1. Thus, in the process described here, the furnace gas eventually consists only of $CO_2$, CO and $H_2$. Consequently, the proportion of CO and the proportion of hydrogen increase according to the equations:

$$C+CO_2 \rightarrow 2CO$$

$$C+H_2O \rightarrow CO+H_2$$

The nascent hydrogen (H) also ensues if the $H_2O$ is introduced into the blast furnace shaft (2) with the metal ore (introduced separately or in the form of damp metal ore) instead of being injected separately through the $H_2O$-inlets 15. Optionally thereby, a portion of the CO gas can be introduced below the surface of the melt.

As an option, pure carbon can be introduced into the melt bath via the C-inlet 18 thereby reducing the melting point of the metal. The carbon being introduced through the C-inlet 18 can come from the same source as the carbon which is introduced into the $CO_2$-converter inlet 20. Preferably, the carbon C comes from the hydrocarbon converter 46 described above.

The portion of the output of the $CO_2$-converter 4 (CO/C aerosol, $H_2$/CO/C aerosol, CO gas) which is not directed into the blast furnace shaft 2 is fed to the further processing converter inlet 28 of the further processing converter 6 in all the exemplary embodiments. Optionally, solids are filtered out before entry into the further processing converter 6.

If the further processing converter 6 is a combustion machine, a combustion process will take place, for example, in a furnace, a gas engine or a gas turbine, or an oxidation process in a fuel cell for example. Necessary additives which are needed for the combustion or oxidation of the gas mixture or the CO gas such as oxygen or air for example are introduced via the additive inlet 29.

If the further processing converter 6 is implemented as a bio converter, then a biological conversion process using microbes or algae runs in the further processing converter 6 according to the following net equations:

$$6CO+3H_2O \rightarrow C_2H_5OH+4CO_2 \quad \text{a)}$$

$$6H_2+2CO_2 \rightarrow C_2H_5OH+3H_2O; \quad \text{b)}$$

$$2CO+4H_2 \rightarrow C_2H_5OH+H_2O. \quad \text{c)}$$

Due to such a biological conversion process using microbes or algae, the gases introduced into the further processing converter 6 can be converted into an end-product such as kerosene, diesel, gasoline, methanol or some other fuel. This end-product is then output through the further processing outlet 32.

If the further processing converter 6 is a CO converter, then a functionalised and/or non-functionalised hydrocarbon is produced in the further processing converter 6. The further processing converter 6 in this case is supplied with CO gas or a $H_2$/CO gas mixture (synthesis gas) from the $CO_2$-converter 4 and with $H_2$ as an additive via the additive inlet 29, this thereby resulting in a synthesis gas with adjustable proportions of $H_2$/CO. Alternatively, CO and $H_2$ are fed together from the outlet 26 of the pipe $CO_2$-converter 4a into the further processing converter 6 when a $H_2$/C-aerosol is fed into the pipe $CO_2$-converter 4a. The hydrocarbons produced thereby are paraffin, kerosene, diesels gasoline, liquid gases or methanol for example. In this case for example, the further processing converter works in accordance with the Fischer Tropsch process, the Bergius Pier process or the Pier process, wherein these processes are known to the skilled person and will not be described in detail here. In this case, the hydrocarbons produced as an end-product are output from the further processing converter outlet 32.

Dependent on the type of further processing converter 6 being used, furnace gas from the second furnace gas outlet 12 can be introduced via the second furnace gas connection 31 into the furnace gas inlet 30 of the further processing converter 6. If the further processing converter 6 is a bio converter as described above, the furnace gas is cleansed of poisonous materials which can harm microbes or algae. If the further processing converter 6 is a CO converter of the type described above, the furnace gas is cleansed of materials which are unsuitable for the operation of the selected CO converter (Fischer Tropsch, Bergius Pier etc.).

The functioning of the exemplary embodiment of the blast furnace 1 shown in FIG. 2 is effected in a similar manner to that described above for the blast furnace according to FIG. 1. The converters shown in FIG. 2 can implement the same operations as those described above.

The above described version (1a) with a pipe $CO_2$-converter 4a comprising a plurality of converter chambers can be used to good effect in the variant of FIG. 2, wherein the converter chambers partially produce a CO/C aerosol which is introduced into the blast furnace shaft 2, and partly a CO gas which is fed to the further processing converter 6. In like manner, the above described version (2) utilising a filter $CO_2$-converter 4b can be used to good effect in the variant of FIG. 2. The CO/C aerosol produced by the filter $CO_2$-converter 4b is introduced together with $H_2O$ into the blast furnace shaft 2 in order to produce nascent hydrogen for the reduction of the metallic oxide. The $H_2$ carrier gas filtered from the $H_2$/C-aerosol is fed into the further processing converter 6, and the CO gas produced in a part of the converter chambers 33 is likewise fed to the further processing converter 6.

The operation of the blast furnace 1 according to FIG. 2 deviates in that the furnace gas which is derived from the first furnace gas outlet 10 is firstly introduced into the combustion machine 36 and then burned in the presence of oxygen. In the case of this combustion process in the combustion machine 36, the inflammable components of the furnace gas are burned, i.e. CO and $H_2$. Carbon monoxide (CO) thereby burns to form carbon dioxide ($CO_2$), and hydrogen ($H_2$) burns to form water vapour ($H_2O$). The proportion of $H_2O$ is very small thereby. The furnace gas is thus fed only indirectly to the $CO_2$-converter 4 since a combustion process takes place first in the combustion machine 36.

As mentioned above, there is still a larger portion of nitrogen ($N_2$) contained in the furnace gas when the blast furnace 1 is being heated up. Nitrogen is an inert gas and does not participate in the combustion process in the combustion machine 36. In the course of further operation, the $N_2$ content in the furnace gas continues to decrease according to the present method since hardly any $N_2$ is introduced into the blast furnace shaft 2 after a certain period of operation. After the combustion of the CO contained in the furnace gas, the exhaust gas mixture emerging from the combustion machine 36 consists for the most part of $CO_2$ namely, the $CO_2$ contained in the furnace gas before the combustion process and the CO that has been burnt to form $CO_2$. This $CO_2$-containing exhaust gas mixture is introduced via the exhaust connection 41 into the $CO_2$-converter gas inlet 22. The $CO_2$-containing exhaust gas is reduced in the presence of C in the $CO_2$-converter 4 as described above.

The further operation of the exemplary embodiment according to FIG. 2 corresponds to the above described operation for FIG. 1 and will not be repeated here.

As was mentioned hereinabove, it should be taken into consideration that a portion of the $CO_2$-containing exhaust gas is optionally fed via the second exhaust gas connection 42 to the further processing converter 6. A desired ratio of CO to $CO_2$ can thus be provided to the further processing converter 6. This is advantageous if the further processing converter 6 is a bio converter which works by the use of microbes or algae.

The operation of the embodiment according to FIG. 3 is effected in a similar manner to that for the embodiment of FIG. 1 described above and will likewise not be repeated in full for the purposes of brevity.

When the blast furnace 1 according to FIG. 3 is in operation, the CO gas or aerosol which is produced in the $CO_2$-converter 4 is fed-out from the second aerosol outlet 24-2 or from the CO outlet 26 and introduced into the combustion machine 36. The thus introduced CO gas or aerosol is burnt in the combustion machine 36 in the presence of oxygen to form $CO_2$. The operation in FIG. 3 differs in that a portion of the CO gas or aerosol from the $CO_2$-converter 4 is only fed indirectly into the further processing converter 6 as a combustion process is initially effected in the combustion machine 36 first. A $CO_2$-containing exhaust gas emerges from the exhaust gas outlet 40 of the combustion machine 36 and is directed via the exhaust gas connection 41 into the further processing converter 6.

In this case, the further processing converter 6 is operating almost entirely with $CO_2$ and appropriate additives which are introduced via the additive inlet 29 and the optionally provided furnace gas inlet 30. The further processing converter 6 in the embodiment of FIG. 3 is a bio converter which works using algae or microbes. Coming into consideration as additives in this exemplary embodiment are preferably hydrogen, water or CO. Hydrogen can be supplied as an additive from a storage tank or from the hydrocarbon converter 46 that was described with reference to FIGS. 4a and 4b. Additionally, CO coming from the portion of the furnace gas which is directed via the second furnace gas outlet 12 and the second furnace gas connection 31 to the further processing converter 6 can be used as an additive. In this case, the substances produced in the biological conversion process, i.e. ethanol ($C_2H_5OH$ or $C_2H_6O$) and $H_2O$ come from the further processing converter outlet 32.

The operation of the blast furnace 1 illustrated in FIG. 4a is effected in a similar manner to that described above for the other exemplary embodiments. The converters shown in FIG. 4a can implement the same operation as was described above. The operation will be described on the basis of a pipe $CO_2$-converter 4a with two converter chambers.

The hydrocarbon converter 46 described above produces C-particles and hydrogen ($H_2$) by decomposing the hydrocarbon. A portion of the hydrogen or the entirety of the hydrogen material can be pre-separated from the C-particles in the hydrocarbon converter 46, for example, under the influence of gravity or by means of a filter. In the embodiment of FIG. 4a, the carbon (C-particles) is introduced alone, or together with a portion of the hydrogen ($H_2$/C-aerosol), via the $CO_2$-converter inlet 20 into the pipe $CO_2$-converter 4a. The remainder of the hydrogen ($H_2$) produced in the hydrocarbon converter 46 is directed in the form of an additive into the additive inlet 29 of the further processing converter of 6.

The hydrocarbon converter 46 operates as follows: hydrocarbon-containing substances are fed into the hydrocarbon converter 46 through the hydrocarbon inlet 48. If the hydrocarbon is methane ($CH_4$) for example, then 1 mol carbon and 2 mol hydrogen are produced from 1 mol methane. The hydrocarbon converter 46 can decompose the introduced hydrocarbon-containing substances by means of a known thermal process, e.g. pyrolysis. Alternatively, the hydrocarbon-containing substances are decomposed by means of a plasma, for example by means of the Kvaerner process. One suitable plasma gas is hydrogen, but any other suitable gases could be used. The hydrocarbons are converted in the decomposition process effected by a plasma in the plasma burner of the hydrocarbon converter 46 at about 1600° C. according to the following reaction equation, wherein the supplied energy for the plasma burner is electricity and the plasma burner produces thermal energy:

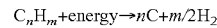

$$C_nH_m + \text{energy} \rightarrow nC + m/2 H_2$$

As a result of the high energy content of the chemical products and the high temperature, the efficiency of the conversion process is almost 100%. The hydrocarbon converter 46 can be used in all of the exemplary embodiments as a source for C-particles or a $H_2$/C-aerosol, and it operates as already described.

The resultant carbon (and optionally hydrogen) is at least partly introduced via the $CO_2$-converter inlet 20 into the pipe $CO_2$-converter 4a. Since the carbon emerging from the hydrocarbon converter 46 has a high temperature, at least a portion of the heat energy of the carbon can be used for heating the conversion process in the pipe $CO_2$-converter 4a which preferably works at a temperature of approx. 1000° C. In the left-hand converter chamber 33a, the C-particles are converted by $CO_2$, which is in molar surplus relative to the C-particles, into a $H_2$/CO/C or CO/C aerosol. In the right-hand converter chamber 33b, the C-particles are converted by $CO_2$ in a molar equilibrium of $CO_2$ and C-particles into CO gas or a $H_2$/CO gas mixture. The $H_2$/CO/C or CO/C aerosol is introduced into the blast furnace shaft 2 together with $H_2O$ and/or through separate inlets in order to produce nascent hydrogen for the reduction of metallic oxide. The introduction of the $H_2O$ is preferably effected through separate inlets.

The operation of the blast furnace 1 illustrated in FIG. 4b is effected in a similar manner to that described above but differs in regard to the operation of the filter $CO_2$-converter 4b. The converters shown in FIG. 4b can work in the same manner as that described above. The operation will be described on the basis of a pipe $CO_2$-converter 4a with two converter chambers (FIGS. 6-9).

The hydrocarbon converter 46 produces C-particles and hydrogen ($H_2$) in the manner described above. In the exemplary embodiment of FIG. 4b, the carbon (C-particle) is introduced into the filter $CO_2$-converter 4b together with the hydrogen in the form of a $H_2$/C-aerosol via the $CO_2$-converter inlet 20. Furthermore, a $CO_2$-containing gas (furnace gas from the blast furnace shaft 2 or exhaust gas from a combustion machine 36) is introduced through the converter gas inlet 22 of the filter $CO_2$-converter 4b.

Firstly, the first converter chamber 33a is supplied via the converter inlet 20 and the aerosol diverting device 45 with a $H_2$/C-aerosol. The $H_2$/C-aerosol has a high temperature such as 1200 to 1800° C. for example in the case of a hydrocarbon converter which works with high temperature plasma. In one case, where the hydrocarbon converter works with thermal energy or with a low temperature plasma, the $H_2$/C-aerosol will have a temperature of at least 300° C. If the $H_2$/C-aerosol is fed into the filter $CO_2$-converter 4b at a temperature of less than 850° C., from an aerosol storage means or a hydrocarbon converter at a lower temperature for example, the $H_2$/C-aerosol is heated to a temperature of over 850° C. before being introduced into the converter chambers 33 or in the converter chambers 33. The hot $H_2$/C-aerosol flows into the first converter chamber 33a and heats it up. The hot carbon-containing C-particles are caught by the filter 39a of the first converter chamber 33a. The longer the $H_2$/C-aerosol is introduced into the first converter chamber 33a, the more carbon-containing C-particles will be deposited in the filter 39a until a desired maximum particle-filling level is reached. The $H_2$ carrier gas filtered out from the $H_2$/C-aerosol is directed by the lead-out device 49 to the carrier gas outlet 27.

As soon as a desired maximum or fixed particle-filling level of the first converter chamber 33a is achieved, the aerosol diverting device 45 switches over and supplies the second converter chamber 33b with the $H_2$/C-aerosol. Due to the supply of the hot $H_2$/C-aerosol, the second converter chamber 33b is heated up in the same way and the filter 39b of the second converter chamber 33b is enriched over time with carbon-containing particles until a desired maximum particle-filling level is reached.

After switching the supply of $H_2$/C-aerosol to the second converter chamber 33b, the $CO_2$-containing gas is directed into the previously filled first converter chamber 33a in order to regenerate it. The introduction of the $CO_2$-containing gas is effected from the converter gas inlet 22 and via the gas diverting device 47, via the gas inlet valves 76 shown in FIGS. 8 and 9 for example. The introduction of the $CO_2$-containing gas can take place in the region of the filter 39a shown in FIGS. 8 and 9 so that the $CO_2$-containing gas flows through the filter 39a in a direction opposite to the flow direction of the $H_2$/C-aerosol and loosens up the previously arrested carbon-containing C-particles in the filter 39a. As a result of the loosening up of the C-particles, there is provided a large reaction surface for rapid and complete reaction of the carbon-containing particles and the $CO_2$-containing gas. The incoming $CO_2$-containing gas (furnace gas, exhaust gas) can be preheated if necessary and has a temperature of 300-1000° C., preferably of approx. 600-900° C. when it is introduced into the converter chamber 33a. A temperature of over 850° C. prevails in the converter chamber 33a during the regeneration process effected by the $CO_2$-containing gas.

The carbon-containing particles (C-particles) are converted into carbon monoxide CO without addition or employment of catalysers in the presence of $CO_2$ according to the equation $C+CO_2 \rightarrow 2CO$. As mentioned above, the molar proportions of carbon C and $CO_2$ in the converter chambers 33a and 33b are dependent on whether a CO/C aerosol or a CO gas is to be produced. Insofar as a molar surplus of C-particles is present in one of the converter chambers 33a, 33b, a CO/C aerosol will be produced and supplied via the aerosol outlet 24 to the blast furnace shaft 2. In accordance with the reactions described above, nascent hydrogen for the reduction of metallic oxide in the blast furnace shaft 2 will then be formed from a CO/C aerosol and $H_2O$. If a molar equilibrium of C-particles and $CO_2$ is present in one of the converter chambers 33a, 33b, a CO gas will be produced in this converter chamber and supplied via the CO outlet 26 to the further processing converter 6. Insofar as a molar surplus of $CO_2$ is present in one of the converter chambers 33a, 33b, a $CO/CO_2$ gas will be produced in this converter chamber and supplied via the CO outlet 26 to the further processing converter 6. In each case, the hydrogen filtered out from the $H_2$/C-aerosol will be fed from the carrier gas outlet 27 to the further processing converter 6.

The introduction of the $CO_2$-containing gas into the respective regenerating converter chamber 33 is effected until a desired minimum particle-filling level is achieved. The desired minimum particle-filling level can be 0%, but does not have to be 0% since it is not always economical to completely convert the C-particles into CO when the system is in operation. The desired minimum particle-filling level can be predetermined on the basis of a fixed cycle time of the change-over between the converter chambers 33. Alternatively, a desired minimum particle-filling level can be specified on the basis of a sensor readout e.g. based on a pressure drop or weight reduction. The magnitudes for the desired maximum and desired minimum particle-filling levels can be determined with the help of the same sensors and devices as described above.

As described above, the converter chambers 33 are arranged alongside one another so that they can be mutually heated by their waste heat. The $CO_2$-containing gas (furnace gas, exhaust gas), $H_2O$ water vapour or another fluid can be fed through the clearance spaces 53 between the converter chambers 33 and/or between the converter chambers 33 and the guide sleeve 51 (FIGS. 6-9). The $CO_2$-containing gas comes from the blast furnace shaft 2 or a combustion machine 36 and has a temperature of more than 200° C. Insofar as the $CO_2$-containing gas is fed through the clearance spaces 53, the $CO_2$-containing gas can be heated still more by the waste heat of the converter chambers 33 so that it will reach a temperature of 600 to 1000°.

In the embodiments of FIGS. 4a and 4b, the connection line 56 between the hydrocarbon converter 46 and the $CO_2$-converter 4 is implemented in such a way that the exiting substances (C-particles and hydrogen) do not cool down too much on the way from the hydrocarbon converter 46 to the $CO_2$-converter 4. Since the substances leaving the hydrocarbon converter 46 (C-particles and hydrogen) have a high temperature, at least a portion of this thermal energy can be used for heating the conversion process in the $CO_2$-converter 4. For example, the connection line 56 can be insulated and/or heated. The hydrogen being produced in the hydrocarbon converter 46 which is not fed to the $CO_2$-converter 4 likewise contains heat energy due to the high operating temperature in the hydrocarbon converter 46. Consequently, this provides one possibility for heating the connection line 56 in that the heat energy of the hydrogen being fed out of the hydrogen outlet 52 is directly or indirectly used for heating the connection line 56 by means of a heat exchanger arrangement. It is thereby possible to convert the hot carbon or the $H_2$/C-aerosol from the hydrocarbon converter 46 into a $H_2$/CO/C or CO/C aerosol (in the left-hand converter chamber with a molar surplus of C-particles) or to convert it into a CO gas (in the right-hand converter chamber with a molar equilibrium of $CO_2$ and C-particles) in the $CO_2$-converter 4 using the warm to hot carbon dioxide of the furnace gas or the $CO_2$-containing exhaust gas without any significant external energy input.

In the embodiments of FIGS. 4a and 4b, the further processing converter 6 may again be a combustion machine, a bio converter or a CO converter for the production of functionalised and/or non-functionalised hydrocarbons as described above in connection with the embodiments of FIGS. 1 to 3. The functioning of the different embodiments of the further processing converter 6 is likewise the same as described above for the other exemplary embodiments.

In all of the exemplary embodiments, a portion of the carbon produced in the hydrocarbon converter 46 which is not needed for the production of an aerosol or CO gas can be derived via the second Coutlet 54 and is either sold as an end-product or introduced via the C-inlet 18 into the blast furnace shaft 2. Alternatively, the carbon can be burned in one of the combustion machines 36 or can be blown into the blast furnace shaft 2 as a reducing agent or used as fuel for the auxiliary heater.

In all of the exemplary embodiments, the gas being directed into the further processing converter 6 can be introduced either directly or be introduced via a mixer which is not shown in the Figures. Thus, for example, in dependence on the desired composition of the synthesis gases, a desired mixing ratio of hydrogen to CO can be established in such a mixer and extracted from a synthesis gas outlet of the mixer. If the entire amount of the available CO-flow and the entire amount of the available $H_2$ flow is not used in the mixer, then the portions of the pure gases CO or $H_2$ that were not funneled into the mixer can each be individually further processed.

In all of the exemplary embodiments, the furnace gas from the second furnace gas outlet 12 may optionally be supplied via the second furnace gas connection 31 to the further processing converter 6. In dependence on which of the further processing converters 6 is used, the furnace gas is pre-cleansed of harmful components.

Likewise applying to all of the exemplary embodiments is that in the event of employment of a combustion machine 36 between the blast furnace shaft 2 and the $CO_2$-converter 4, a portion of the $CO_2$-containing exhaust gas can be supplied directly, i.e. by-passing the $CO_2$-converter 4, via the second exhaust connection 42 to the further processing converter 6.

Insofar as the hydrocarbon converter 46 produces additional $H_2$ gas which cannot be converted in the $CO_2$-converter with $CO_2$, then this $H_2$ can be stored and sold as an end-product. Alternatively, such surplus $H_2$ can be used in order to operate the above mentioned auxiliary heater for the blast furnace shaft 2.

The carbon that was produced by the hydrocarbon converter 46 but not used can be sold as an end-product such as carbon, carbon black or activated charcoal. As an alternative or in addition thereto, surplus carbon can be introduced partially via the C inlet 18 into the molten bath in order to lower its melting point. Furthermore, the thus produced carbon could also be used for heating the auxiliary heater or the blast furnace shaft 2.

In all of the exemplary embodiments, the blast furnace shaft 2 or the $CO_2$-converter 4 can be additional heated by the heat from an auxiliary heater. The temperature in the lower part of the blast furnace shaft 2 should be sufficient to hold the metal in the molten state. The temperature inside the $CO_2$-converter 4 should be sufficient to achieve as complete a conversion of $CO_2$ into CO as possible. The heat for the auxiliary heater is preferably produced from the combustion process in one of the combustion machines 36 or in a further processing converter 6 in the form of a combustion machine or is extracted from the process heat of the CO-converter. Alternatively, waste heat resulting from the operation of the hydrocarbon converter 46 can be used. As mentioned above, the hydrocarbon converter 46 works at high temperatures especially when it is implemented in the form of a high temperature plasma converter. This waste heat can, for example be supplied to the blast furnace shaft 2 and/or to the $CO_2$-converter 4 by means of heat exchangers or mutually passing flows of material (in the clearance spaces 53 of the guide sleeve 51).

If a hydrocarbon converter 46 of low temperature type is used (e.g. a thermal energy or low-temperature plasma type), it is only necessary to operate an auxiliary heater on the $CO_2$-converter 4 if the conversion of $CO_2$ into CO would otherwise be incomplete because of too low an operating temperature (i.e. under 800° C.) in the $CO_2$-converter 4, i.e. too little $CO_2$ is converted into CO. Whereas at temperatures of 800° C. about 94% carbon monoxide would still be supplied, the conversion rate below this temperature drops rapidly. Since about 99% carbon monoxide can be supplied at temperatures of around 1000° C., it would be less useful to heat the $CO_2$-converter 4 up much further (e.g. to 1700° C.) since half the thermal energy would be lost due to the emission of CO gas through the second CO outlet 26. A temperature of 1000° C. to 1300° C. should be present in at least the lower region of the blast furnace shaft 2 so that the reduced metal (pig iron) is then molten and can be discharged or tapped off. If the blast furnace shaft 2 is not heated sufficiently by the hot CO gas being introduced and lower temperatures are occurring, it would be helpful to operate an auxiliary heater for the blast furnace shaft 2. The auxiliary heater could also be an induction heater.

If a hydrocarbon converter 46 of high temperature type is used, the hydrocarbon converter 46 will already be supplying carbon or a $H_2$/C-aerosol at 900° C. to 1700° C. (in the case of a high temperature plasma reactor, 1500° C. to 1700° C.) to the $CO_2$-converter 4. An operating temperature for the $CO_2$-converter 4 of up to 1700° C. thus becomes reasonable. An auxiliary heater for the $CO_2$-converter 4 would not be necessary in this case.

It should be taken into consideration that, depending upon the size of the plant, a plurality of hydrocarbon converters 46 could be operated in parallel in order to provide the desired conversion capacity. In all of the embodiments, the hydrocarbon converter 46 can be a combination of a plurality of hydrocarbon converters 46a, 46b operating in parallel as shown in FIG. 5, such as a combination of a high temperature hydrocarbon converter 46a and a low-temperature hydrocarbon converter 46b for example. A high temperature hydrocarbon converter works at temperatures of more than 1000° C. and a low-temperature hydrocarbon converter works at temperatures of between 200 and 1000° C. The hydrocarbon that is to be decomposed can be supplied to the high temperature and the low-temperature hydrocarbon converters 46a, 46b via a common inlet or through separate inlets. A hydrocarbon converter 46 consisting of a plurality of smaller modules has the advantage that different hydrocarbons or differing proportions of hydrocarbons can be decomposed under ideal process parameters. Furthermore, the individual high temperature or low-temperature hydrocarbon converters can produce different grades or types of carbon, for example, for sale and for use in the blast furnace shaft.

The embodiments described above been described for ideal conditions. It will be clear to the skilled person that in practice varying proportions of hydrogen, $CO_2$, CO and $N_2$ will be present in the furnace gas. Consequently, varying streams of CO gas or synthesis gas will also be discharged from the $CO_2$-converters 4, 4a, 4b. Nevertheless, the composition of a synthesis gas which is to be processed in the further processing converter 6 can be kept constant with the help of a mixer. Consequently, a synthesis gas having a virtually constant composition can be provided to the further processing converter 6.

In the case of a further processing converter 6 using microbes or algae however, the slight fluctuations in the gas mixture being fed in can be compensated for by the microbes or the algae.

To recapitulate, it may be said that the speed of reduction of the metal ore is increased in the blast furnace and process described here for the treatment of metal ores. Basically, there is only a limited time available for the process of reducing the metal ore in the blast furnace. This time is determined by the period spent (path-length over speed) by the iron ore in the blast furnace. According to calculations made by the inventor, two thirds of the gas volumes fed into the blast furnace and a third of the emerging furnace gas are saved compared with the process mentioned hereinabove in connection with German patent application No. 10 2013 009 993.

For the following reasons, special advantages result for the production of iron and steel. Iron Fe is a non-noble metal, i.e. Fe(II) cannot oxidize hydrogen, or differently expressed: hydrogen cannot reduce Fe(II) to iron. Nevertheless, hydrogen can reduce Fe(III) to Fe(II) in certain circumstances. Furthermore, molecular hydrogen reduces Fe(III) faster than CO. Nascent hydrogen reduces still better than molecular hydrogen. Nascent hydrogen or hydrogen in stade nascendi is atomic hydrogen which is much more reactive than molecular hydrogen immediately after it has been formed but into which it is converted after a short time. In the method being described here, an aerosol consisting of a carrier gas (CO or a mixture of CO and $H_2$) and carbon particles (C-particles) is produced which can be introduced via the blast jets into the blast furnace shaft. In addition, water vapour can be injected. Consequently, the following reaction occurs in the presence of FeOx:

$$C+H_2O \rightarrow 2H+CO$$

The hydrogen can thus react immediately:

$$Fe_2O_3+2H \rightarrow 2FeO+H_2O$$

The FeO is then reduced by the likewise present CO:

$$FeO+CO \rightarrow Fe+CO_2$$

Only a little amount of water has to be injected since the reduction of Fe(III) generates further water. It is thereby possible to increase either the capacity of the blast furnace or reduce its size.

As a modification, water vapour $H_2O$ can also be added to a CO/C aerosol before being introduced into the blast furnace shaft 2. A $H_2$/CO/C aerosol thereby results.

As a further modification, a CO/C aerosol can be completely converted with water vapour $H_2O$. A hydrogen-poor synthesis gas CO/$H_2$ thereby ensues As a further modification which is possible for all the blast furnaces of FIGS. 1-4b, the production of a CO/$H_2$ gas mixture from C and $H_2O$ in the $CO_2$-converters can be considered.

The invention has been described on the basis of preferred exemplary embodiments, wherein individual features of the described exemplary embodiments may be combined freely with one another and/or may be substituted insofar as these features are compatible. Furthermore, individual features of the described embodiments may be omitted insofar as these features are not essential. Numerous modifications and practical implementations are possible and obvious to those skilled in the art without thereby departing from the full scope of the present invention.

The invention claimed is:

1. A method for processing metal ore comprising the following steps:
    reducing a metal ore in a blast furnace shaft;
    producing furnace gas containing $CO_2$, in the blast furnace shaft;
    discharging the furnace gas from the blast furnace shaft;
    directing the furnace gas directly or indirectly into a $CO_2$-converter and converting the $CO_2$ contained in the furnace gas into an aerosol consisting of a carrier gas and C-particles in the $CO_2$-converter in the presence of a stoichiometric surplus of C;
    directing a first portion of the aerosol from the $CO_2$-converter into the blast furnace shaft;
    wherein a second portion of the aerosol from the $CO_2$-converter is fed to a further processing process; or wherein the second portion of the aerosol from the $CO_2$-converter is first burned to form a $CO_2$-containing exhaust gas mixture before it is passed on as this exhaust gas mixture to the further processing process; and
    introducing water vapour $H_2O$ into the blast furnace shaft, wherein the step of directing a first portion of the aerosol from the $CO_2$-converter into the blast furnace shaft and the step of introducing the water vapour into the blast furnace shaft are effected via separate nozzles;
    wherein the further processing process is selected from the group consisting of:
    an oxidation process in a fuel cell,
    a combustion process in a gas engine,
    a combustion process in a gas turbine,
    a biological conversion process in a bio converter and is carried out using microbes or algae according to one or more of the following net equations:

a) $6CO+3H_2O \rightarrow C_2H_5OH+4CO_2$;

b) $6H_2+2CO_2 \rightarrow C_2H_5OH+3H_2O$;

c) $2CO+4H_2 \rightarrow C_2H_5OH +H_2O$; and a conversion process in which synthesis gas is converted into at least one of a functionalised and a non-functionalised hydrocarbon.

2. The method according to claim 1, wherein water vapour $H_2O$ is added to the aerosol before directing it into the blast furnace shaft.

3. The method according to claim 2, wherein as much water vapour $H_2O$ is added to the aerosol as to a produce a hydrogen-poor synthesis gas CO/$H_2$ before being directed into the blast furnace.

4. The method according to claim 1, wherein, in the case of indirect introduction into the $CO_2$-converter, the furnace gas is first burned to form a $CO_2$-containing exhaust gas mixture before being passed on as this exhaust gas mixture to the $CO_2$-converter and is converted in the $CO_2$-converter.

5. The method according to claim 4, which comprises the further step of directing a portion of the $CO_2$-containing exhaust gas mixture past the $CO_2$-converter to a further processing process.

6. The method according to claim 1, wherein molten metal is formed in the blast furnace shaft by reducing the metal ore during the operation of the method, and wherein additional carbon is introduced into the lower region of the blast furnace shaft in contact with the molten metal.

7. The method according to claim 1, wherein the conversion of $CO_2$ into an aerosol in the $CO_2$-converter takes place at a temperature of 800 to 1700° C.

8. The method according to claim 1, wherein the $CO_2$-converter comprises a plurality of alternately operative converter chambers,
- wherein the conversion of $CO_2$ in a first converter chamber is implemented with a stoichiometric surplus of C so that an aerosol with C-particles is formed; and
- wherein the conversion of $CO_2$ in a second converter chamber is implemented with a stoichiometric equilibrium of C and $CO_2$ or with a stoichiometric surplus of $CO_2$ so that a CO gas or a $CO_2$/CO gas mixture without C-particles is formed.

9. The method according to claim 1, wherein the $CO_2$-converter comprises a plurality of converter chambers which can be filled between a desired minimum and a desired maximum particle-filling level, wherein the conversion of the $CO_2$ contained in the furnace gas into an aerosol comprises the following steps:
- supplying a first part of the converter chambers with a $H_2$/C-aerosol consisting essentially of hydrogen and carbon-containing particles until the converter chambers being supplied are filled to the desired maximum particle-filling level;
- supplying a second part of the converter chambers with the $H_2$/C-aerosol as soon as the desired maximum particle-filling level of the first part of the converter chambers is reached; and
- directing $CO_2$ into the first part of the converter chambers that are filled with carbon-containing particles,
- wherein the carbon is converted into carbon monoxide according to the equation $C + CO_2 \rightarrow 2CO$.

10. The method according to claim 1, wherein the further processing process is a biological conversion process which comprises the further following steps:
- decomposing a fluid containing hydrocarbon into carbon and hydrogen
  a) by means of a plasma or
  b) by introducing thermal energy,
  wherein the decomposing step is preferably carried out in a separate hydrocarbon converter; and
- supplying said hydrogen ($H_2$) to the biological conversion process.

11. The method according to claim 1, wherein the synthesis gas is produced by the following steps:
- decomposing a fluid containing hydrocarbons into carbon (C) and hydrogen ($H_2$)
  a) by means of a plasma or
  b) by introducing thermal energy; and
- mixing at least a portion of the hydrogen ($H_2$) with at least a portion of the CO component in the aerosol that was produced in the $CO_2$-converter.

12. The method according to claim 1, wherein the carrier gas of the aerosol produced in the $CO_2$-converter consists essentially of CO or of a mixture of CO and $H_2$.

\* \* \* \* \*